United States Patent [19]
McCarthy et al.

[11] Patent Number: 5,795,905
[45] Date of Patent: Aug. 18, 1998

[54] CRF RECEPTOR ANTAGONISTS AND METHODS RELATING THERETO

[75] Inventors: James R. McCarthy, Solana Beach; Yun Feng Xie, Carlsbad; Jeffrey P. Whitten, San Diego; Thomas R. Webb, Olivenhain; Chen Chen, San Diego, all of Calif.; John Y. Ramphal, Lafayette, Colo.

[73] Assignee: Neurocrine Biosciences, Inc., San Diego, Calif.

[21] Appl. No.: 468,799

[22] Filed: Jun. 6, 1995

[51] Int. Cl.$^6$ .................... A61K 31/41; C07D 249/14
[52] U.S. Cl. ............... 514/383; 548/262.8; 548/264.8; 548/265.8
[58] Field of Search ............ 548/262.8, 264.8, 548/265.8; 514/383, 340, 256, 307, 314, 266; 546/272.4, 144, 167; 544/333, 277

[56] References Cited

U.S. PATENT DOCUMENTS

| | | | |
|---|---|---|---|
| 3,515,723 | 6/1970 | Cragoe | 260/250 |
| 4,605,642 | 8/1986 | Rivier | 514/12 |
| 5,036,085 | 7/1991 | Heinemann et al. | 514/361 |
| 5,063,245 | 11/1991 | Abreu et al. | 514/404 |
| 5,322,949 | 6/1994 | Heinemann et al. | 548/128 |
| 5,376,670 | 12/1994 | Connor et al. | 514/383 |
| 5,434,267 | 7/1995 | Kraus et al. | 546/301 |
| 5,464,847 | 11/1995 | Courtemanche et al. | 514/342 |
| 5,470,855 | 11/1995 | Bernat et al. | 514/236.8 |

FOREIGN PATENT DOCUMENTS

| | | |
|---|---|---|
| 2138638 A1 | 6/1995 | Canada . |
| 389 901 A1 | 10/1990 | European Pat. Off. . |
| 473 980 A1 | 3/1992 | European Pat. Off. . |
| 548 650 A1 | 6/1993 | European Pat. Off. . |
| 576 350 A1 | 12/1993 | European Pat. Off. . |
| 659 747 A1 | 6/1995 | European Pat. Off. . |
| 2202385 | 7/1973 | Germany . |
| WO 91/09857 | 7/1991 | WIPO . |

OTHER PUBLICATIONS

Whitfield et al., Heterocycles from N–benzoylthioamides and dinucleophilic reagents, J. Heterocyclic Chemistry, vol. 18(6), pp. 1197–1201, 1981.

Elslager et al., "Synthesis of 5,5'–{|3–(Dimethylamino)propyl]imino}bis[3–(trichloromethyl)–1,2,4–thiadiazole]and Related Thiadiazoles as Antimalarial Agents," *Journal of Heterocyclic Chemistry* 10(4): 611–622, 1973.

Yonemoto and Shibuya, "Decomposition Reaction of 3–Aryl–6–disubstituted Amino–1,4,2,5–dithiadiazines in the Solid State," *Bull. Chem. Soc. Jpn.* 62: 2407–2409, 1989.

DATABASE CROSSFIRE, Beilstein Informationssysteme GmbH, Beilstein Record No. 669870, 1962.

Ried et al., Synthesis of new potentially analgesic and antibiotic pyradazino[4,3–e][1,3]oxazinones and pyramido [4,5–c]pyradazinones, Chemical Abstract, 110:23826c, pp. 547, 1989.

Stein, N–substituted amino–1,2,4–triazoles from 2–amino–1,3,4–oxadiazoles and secondary amines, Chemical Abstract 86:43626b, pp. 529, 1977.

Shepard et al., Pyrazine diuretics. VI. (Pyrazinecarboxamido)guanidines, J. Med. Chem., vol. 12, pp. 280–5, 1969.

Okide, Synthesis of five–and six–membered nitrogen heterocycles from 1–chloro–2–azapropenylium and 1–chloro–2,4–diazabutenylium salts, Indian Journal of Chemistry, vol. 32B, pp. 422–6, 1993.

*Primary Examiner*—Mukund J. Shah
*Assistant Examiner*—Deepak R. Ray
*Attorney, Agent, or Firm*—Seed and Berry

[57] ABSTRACT

CRF receptor antagonists are disclosed. Such receptor antagonists are thiadiazole-, pyrimidine-, triazine-, and triazole-containing compounds substituted with both a C3–C14 monocyclic or fused, homoaryl or heteroaryl group and a substituted amine group. The CFR receptor antagonists have utility in the treatment of a variety of disorders, including disorders associated with the hypersecretion of CRF.

54 Claims, No Drawings

CRF RECEPTOR ANTAGONISTS AND METHODS RELATING THERETO

TECHNICAL FIELD

This invention relates generally to CRF receptor antagonists, and more specifically, to thiadiazole-, pyrimidine-, triazine-, and triazole-containing compounds for use as CRF receptor antagonists.

BACKGROUND OF THE INVENTION

The first corticotropin-releasing factor (CRF) was isolated from ovine hypothalmi and identified as a 41-amino acid peptide (Vale et al., *Science* 213:1394–1397, 1987). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 224:1449–1451, 1984, pituitary (DeSouza et al., *Methods Enzymol.* 124:560, 1986; Wynn et al., *Biochem. Biophys. Res. Comm.* 110:602–608, 1983), adrenals (Udeltsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118:1171–1179, 1986) which mediates CRF-stimulated increase in intracellular production of cAMP (Bilezikjian, L. M., and W. W. Vale, *Endocrinology* 113:657–662, 1983). The receptor for CRF has now been cloned from rat (Perrin et al., *Endo* 133(6):3058–3061, 1993), and human brain (Chen et al., *PNAS* 90(19):8967–8971, 1993; Vita et al., *FEBS* 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J Physiol.* 255:R744, 1988). Furthermore, clinical data suggests that CRF may be hypersecreted in the brain in depression, anxiety-related disorders, and anorexia nervosa. (DeSouza. *Ann. Reports in Med. Chem.* 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyrazoline derivatives (Abreu et al., U.S. Pat. No. 5,063, 245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1–10 μM range and 0.1–10 μM range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically, to thiadiazole-, pyrimidine-, triazine-, and triazole-containing compounds for use as CRF receptor antagonists. The CRF receptor antagonists of this invention have the following general structures I through VI:

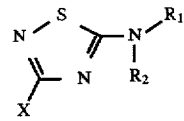

I

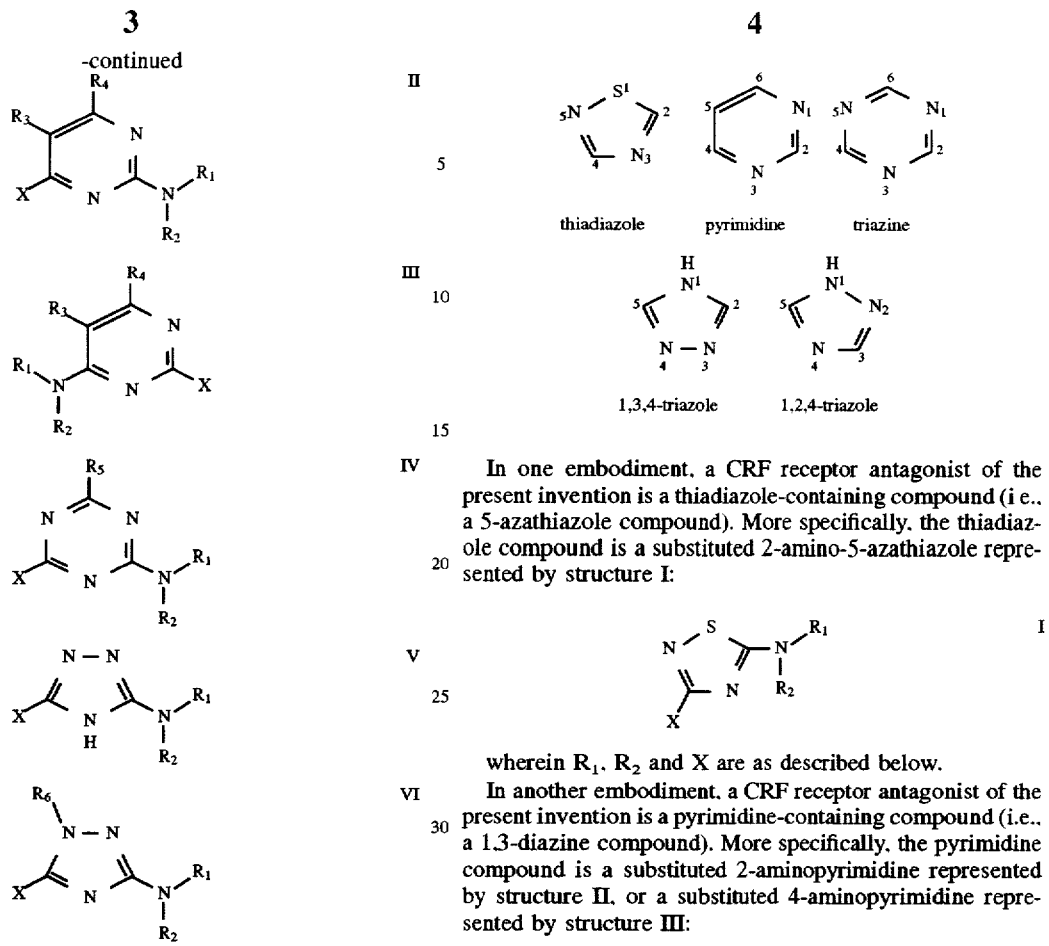

where $R_1$ through $R_6$ and X are as identified in the following detailed description.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to substituted heteroaromatic compounds useful as corticotropin-releasing factor (CRF) receptor antagonists. More specifically, this invention is directed to CRF receptor antagonists derived from thiadiazole (i.e., 5-azathiazole), pyrimidine, (i.e., 1,3-diazine), triazine (i.e., 1,3,5-triazine), and triazine), and triazole (i.e., 1,3,4-triazole and 1,2,4-triazole). The structural formulas and atom numbering of these parent compounds is shown below:

In one embodiment, a CRF receptor antagonist of the present invention is a thiadiazole-containing compound (i.e., a 5-azathiazole compound). More specifically, the thiadiazole compound is a substituted 2-amino-5-azathiazole represented by structure I:

wherein $R_1$, $R_2$ and X are as described below.

In another embodiment, a CRF receptor antagonist of the present invention is a pyrimidine-containing compound (i.e., a 1,3-diazine compound). More specifically, the pyrimidine compound is a substituted 2-aminopyrimidine represented by structure II, or a substituted 4-aminopyrimidine represented by structure III:

wherein $R_1$, $R_2$, $R_3$, $R_4$ and X are as described below.

In a further embodiment, a CRF receptor antagonist of the present invention is a triazine-containing compound (i.e., a 1,3,5-triazine compound). More specifically, the triazine compound is a substituted 2-aminotriazine compound represented by structure IV:

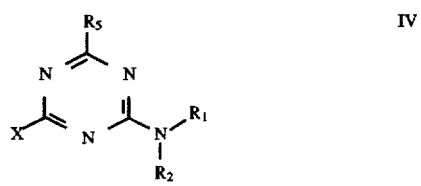

wherein $R_1$, $R_2$, $R_5$, and X are as described below.

In still a further embodiment, a CRF receptor antagonist of the present invention is a triazole-containing compound. More specifically, the triazole compound is a substituted 2-amino-1,3,4-triazole represented by structure V, or a substituted 3-amino-1,2,4-triazole represented by structure VI:

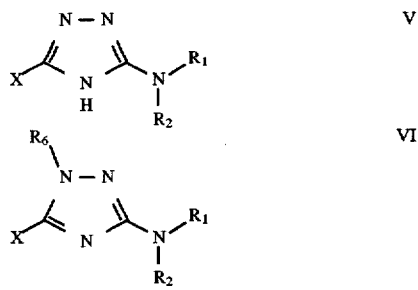

wherein $R_1$, $R_2$, $R_6$, and X are as described below.

The X moieties of structures I through VI are selected from substituted monocyclic and fused, homoaryl and heteroaryl groups. As used herein, the term "homoaryl" refers to an aromatic compound having an aromatic ring made up of only carbon atoms, while the term "heteroaryl" refers to an aromatic compound having an aromatic ring which contains, in addition to carbon, one or more other atoms, most commonly nitrogen, oxygen and sulfur. The terms homoaryl and heteroaryl are collectively referred to herein as "aryl" groups. The term "monocyclic aryl" refers to an aromatic compound having a single aromatic ring, while the term "fused aryl" refers to aromatic rings that share a pair of carbon atoms, and includes multiple fused aromatic rings. Lastly, the term "substituted aryl" refers to an aromatic compound having at least one ring hydrogen substituted with another atom.

The monocyclic and fused, homoaryl and heteroaryl groups of this invention may contain (excluding heteroatoms and carbons attributable to aryl substitutions) from 3 to 14 carbon atoms. Accordingly, the aryl groups of this invention are referred to herein as "C3–C14 monocyclic and fused, homoaryl and heteroaryl groups." Representative examples of such groups include (but are not limited to) phenyl, pyridyl, pyrimidyl, thiophenyl, naphthalenyl, quinolinyl, isoquinolinyl, purinyl, pyrrolyl, furanyl, thiophenyl, thiazolyl and imidazolyl.

The C3–C14 monocyclic and fused, homoaryl and heteroaryl groups of the present invention are substituted with one (or more) substituents. To this end, the C3–C14 monocyclic and fused, homoaryl and heteroaryl groups may be substituted at any available ring position, and may be substituted with more than one substituent. For multiply substituted C3–C14 monocyclic and fused, homoaryl and heteroaryl groups, the individual substituents may be the same or different.

Suitable substituents of the C3–C14 monocyclic and fused, homoaryl and heteroaryl groups include (but are not limited to) hydroxy, halogens (chlorine, bromine, fluorine and iodine), C1–C8 alkyl groups (such as methyl and ethyl), C1–C8 alkoxy groups (such as methoxy, ethoxy, propyloxy and isopropoxy), C1–C8 thioalkyl groups (such as thiomethyl and thioethyl), C3–C8 cycloalkyl groups (such as cyclopropyl and cyclohexyl), C3–C8 heterocyclic alkyl groups (such as morpholinyl, piperidinyl, tetrahydrofuranyl and tetrahydropyranyl), amino, C1–C8 substituted amine (such as methylamino, ethylamino and dimethylamino), cyano, C1–C8 alkylcyano, C1–C8 alkylsulfoxidyl (such as methylsulfoxidyl) and C1–C8 alkylsulfonyl (such as methyl sulfonyl).

Moreover, suitable substituents include C3–C14 monocyclic and fused, homoaryl and heteroaryl groups as defined above (such as phenyl), as well as aryloxy groups (such as phenoxy), arylsulfoxidyl groups (such as phenylsulfoxidyl), arylsulfonyl groups (such as phenylsulfonyl), arylalkyl groups (such as benzyl and ethylphenyl) and arylalkyloxy groups (such as benzyloxy) where the alkyl group of the arylalkyl and arylalkyloxy groups is a C1–C8 alkyl group and the aryl moiety of the aryloxy, arylsulfoxidyl, arylsulfonyl, arylalkyl and arylalkyloxy groups is a C3–C14 monocyclic and fused, homoaryl and heteroaryl group. Substituted C3–C14 monocyclic and fused, homoaryl and heteroaryl groups as defined above may also be used as substituents.

Furthermore, halogenated derivatives of the above alkyl-containing substituents are also within the scope of this invention, including (but not limited to) halogenated C1–C8 alkyl and alkoxy groups (such as trifluoromethyl and trifluoromethoxy).

In a preferred embodiment, the substituents for the C3–C14 monocyclic and fused, homoaryl and heteroaryl groups are selected from chloro, bromo, fluoro, methyl, trifluoromethyl, methoxy, ethoxy, benzyloxy, cyano, sulfoxidyl, sulfonyl, amino, substituted amino, trifluoromethoxy and thiomethyl groups.

In a further preferred embodiment, the C3–C14 monocyclic and fused, homoaryl and heteroaryl groups are multiply substituted phenyl groups, wherein the substituents are independently selected from a halogen and methoxy, including (but not limited to) 2,4-dichlorophenyl, 2,4,6-trichlorophenyl, 2,4-dimethoxyphenyl, 2,6-dimethoxyphenyl, 2,4,6-trimethoxyphenyl, 2-methoxy-4-chlorophenyl, 2,4-dimethoxy-6-chlorophenyl, 2,6-dimethoxy-4-chlorophenyl, 2,5-dimethoxy-4-methylphenyl, 2,4-dimethyl-6-methoxyphenyl and 2,4,6-trimethoxyphenyl. In yet a further embodiment, the multiply substituted phenyl group is 4-cyano-2,6-dimethylphenyl.

For the pyrimidine-containing compounds of structure II, the X moiety may be fused to the pyrimidine ring at both the X and $R_3$ positions. In this case, the X moiety is a substituted C3–C14 monocyclic or fused, homoaryl or heteroaryl group, and substituted with $R_3$ which, in turn, is fused to the 5-position of the pyrimidine ring and joined to the X moiety via a methylene, oxygen or sulfur linkage as represented by the following structure II:

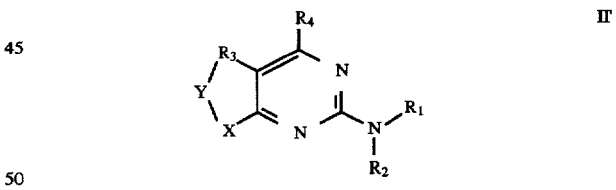

where Y is selected from —$CH_2$—, —O— and —S—; X is as defined above; and $R_1$, $R_2$, $R_3$ and $R_4$ are as defined below. In a preferred embodiment, structure II has the following structure II":

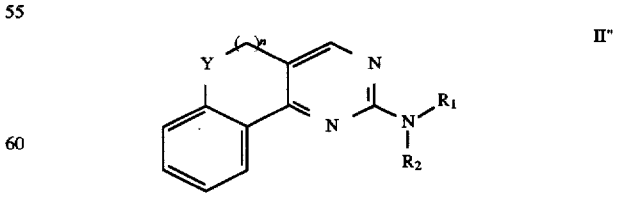

where Y is selected from —$CH_2$—, —O—and —S—; n=0–3; $R_1$ and $R_2$ are as defined below; and the phenyl group is further substituted with one or more of the substituents for the C3–C14 monocyclic and fused, homoaryl or heteroaryl groups identified above, including (but not limited to) halogens (such as chloro) and C1–C8 alkoxy groups (such as methoxy).

The CRF receptor antagonists of structures I through VI are further substituted with an amino group bearing substituents $R_1$ and $R_2$ (i.e., $-NR_1R_2$). The amino substituents $R_1$ and $R_2$ may be the same or different, and are independently selected from the following groups:

C1–C6 alkyl groups, including (but not limited to) branched or straight chain alkyl groups such as methyl, ethyl, n-propyl, n-butyl, n-pentyl, n-hexyl and isopropyl;

C3–C6 alkenyl groups, including (but not limited to) propenyl ($-CH_2CH=CH_2$) and butenyl ($-CH_2CH_2CH=CH_2$ and $-CH_2CH=CHCH_3$);

C2–C6 alkylether and alkylthioether groups, including (but not limited to) ethylmethylether ($-CH_2CH_2OCH_3$), ethylmethylthioether ($-CH_2CH_2SCH_3$), ethylether ($-CH_2CH_2OCH_2CH_3$), ethylthioether ($-CH_2CH_2SCH_2CH_3$), propylmethylether ($CH_2CH_2CH_2OCH_3$) and propylmethylthioether ($CH_2CH_2CH_2SCH_3$);

C4–C9 cycloalkylalkyl groups, including (but not limited to) cyclorwpylmethyl, cyclopropylethyl and cyclopropylpropyl;

C7–C20 dicycloalkylalkyl groups, including (but not limited to) dicyclopropylmethyl, dicyclopropylpropyl, cyclopropyl cyclohexyl methyl, dicyclohexylmethyl, dicyclohexylethyl, dicyclohexylpropyl and cyclopropyl cyclobutylmethyl;

C7–C20 cycloalkylarylalkyl groups, including (but not limited to) cyclopropylphenylmethyl and cyclopropyl-β-naphthalenylmethyl;

C7–C20 arylalkyl groups, including (but not limited to) benzyl and β-methylenenaphthalene;

C7–C20 diarylalkyl groups, including (but not limited to) diphenylmethyl; and

C3–C14 monocyclic and fused heteroaryl and heteroarylalkyl groups, including (but not limited to) pyridyl, methylpyridyl, imidazolyl, methylimidazolyl, furanyl and methylfuranyl.

With respect to the above-identified $R_1$ and $R_2$ moieties, the aryl portion of the cycloalkylarylalkyl groups, arylalkyl groups and diarylalkyl groups are selected from C3–C14 monocyclic and fused, homoaryl and heteroaryl groups as defined above, including (but not limited to) phenyl, pyridyl, imidazolyl and furanyl. Furthermore, the alkyl portion of the cycloalkylalkyl groups, dicycloalkylalkyl groups, cycloalkylarylalkyl groups, arylalkyl groups, diarylalkyl groups and heteroarylalkyl groups are C1–C6 alkyl groups, and the cycloalkyl portion of the cycloalkylalkyl groups, dicycloalkylalkyl and cycloalkylarylalkyl groups are C3–C8 cycloalkyl groups.

The $R_1$ and $R_2$ moieties identified above may also be substituted (referred to herein as "substituted derivatives" of $R_1$ and $R_2$). With regard to the aryl portion of the cycloalkylarylalkyl groups, arylalkyl groups and diarylalkyl groups, such derivatives include substituted C3–C14 monocyclic and fused, homoaryl and heteroaryl groups as defined above. In addition, the alkyl groups, alkenyl groups, and alkyl ether and thioether groups, as well as the alkyl portion of the cycloalkylalkvl groups, dicycloalkylalkyl groups, cycloalkylarylalkyl groups, arylalkyl groups, diarylalkyl groups and heteroarylalkyl groups, may also be substituted with one or more of the substituents identified above with respect to the C3–C14 monocyclic and fused, homoaryl and heteroaryl groups. For example, the C1–C6 alkyl groups may be substituted with a C1–C8 alkoxy group to yield alkoxy substituted alkyl moieties such as 4-methoxybutyl and 3-ethoxypropyl, or may be substituted with fluorine to yield C1–C6 trifluoromethyl alkyl groups. Furthermore, the cycloalkyl portion of the cycloalkylalkyl, dicycloalkylalkvl and cycloalkylarylalkly groups may be one or more heterocyclic alkyl groups, such as tetrahydropyranyl, tetrahydrofuranyl, tetrahydrothiophenyl, tetrahydrothiopyranyl, oxatanyl, thiooxatanyl, piperidinyl, pyrrolidinyl, morpholinyl and piperazinyl.

In one embodiment of this invention, at least $R_1$ or $R_2$ (or both) have pi (i.e., $\pi$) character—that is, have atomic or molecular orbitals capable of forming $\pi$ bonds. Suitable moieties which possess such $\pi$ character include (but are not limited to) unsaturated moieties such as alkenyl and aryl moieties, and saturated moieties including cyclopropyl moieties. Accordingly, in one embodiment of this invention, $R_1$ and/or $R_2$ have $\pi$ character.

In a further embodiment, $R_1$ is a straight chain C1–C6 alkyl group, and $R_2$ is a branched C1–C6 alkyl group or a C4–C9 cycloalkylalkyl group. In a preferred embodiment, $R_1$ is n-propyl and $R_2$ is dicyclopropylmethyl.

In addition to substituents $R_1$, $R_2$ and X as defined above, the compounds of structures II and III are further substituted with an $R_3$ and $R_4$ moiety. Substituents $R_3$ and $R_4$ may be the same or different, and are independently selected from hydrogen; amino; C1–C8 substituted amine groups including (but not limited to) methylamino, ethylamino and dimethylamino; halogen including (but not limited to) fluoro and chloro; C1–C2 alkyl groups including methyl and ethyl; C1–C6 carbonyl-containing groups such as esters and amides, including (but not limited to) methyl ester, dimethyl amide, and acetamide; and C1–C6 sulfur-containing groups such as sulfones and sulfoxides including (but not limited to) methyl sulfonyl and methyl sulfoxy. In one embodiment $R_3$ and $R_4$ are both hydrogen, and in another embodiment $R_3$ is methyl and $R_4$ is hydrogen.

With regard to structure IV, $R_1$, $R_2$ and X are as defined above and $R_5$ is selected from hydrogen, halogen, amino, C1–C6 alkyl groups, and C1–C6 alkoxy groups. In a preferred embodiment, $R_5$ is an amino group.

Lastly, with respect to structures V and VI, $R_1$, $R_2$ and X are as defined above, and $R_6$ of structure VI is selected from hydrogen and methyl.

The compounds of the present invention may be prepared by a variety of synthetic methods including those described in more detail in the Examples. In particular, the thiadiazole-containing compounds may be prepared by Method A as described in Example 1; the pyrimidine-containing compounds may be prepared by Methods B through E as described in Example 2; and the triazine-containing compounds may be prepared by Methods F and G as described in Example 3; and the triazole-containing compounds may be prepared by Method H as described in Example 4. For purpose of clarity, these methods of preparation (i.e. Methods A through H) are briefly summarized below.

The thiadiazole-containing compounds of formula I may be prepared by the reaction scheme of Method A.

Method A:

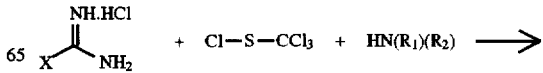

-continued
Method A:

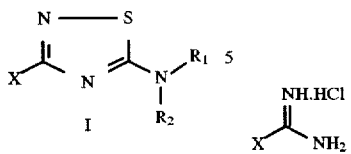

In this method, reaction of an appropriately substituted amidine with perchloromethyl mercaptan, followed by treatment with a suitable amine, provides a substituted 2-amino-4-aryl thiadiazole compound of formula I.

The pyrimidine-containing compounds of formula II and III may be prepared by the reaction scheme of Methods B through E.

Method B:

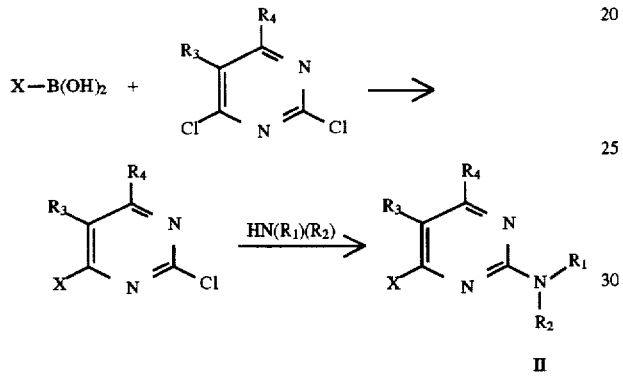

In this method, treatment of a 2,4-dichloropyrimidine compound with an appropriately substituted aryl boronic acid provides a 2-chloro-4-arylpyrimidine compound which, upon reaction with a suitable amine, produces a substituted 2-amino-4-arylpyrimidine compound of formula II. (It should be noted that, by reversing the sequence of reactions (i.e., reaction of a 2,4-dichloropyrimidine compound with a suitable amine, followed by reaction with an appropriately substituted aryl boronic acid), this method may also be used to prepare substituted 2-aryl-4-aminopyrimidine compounds of formula III.)

Method C:

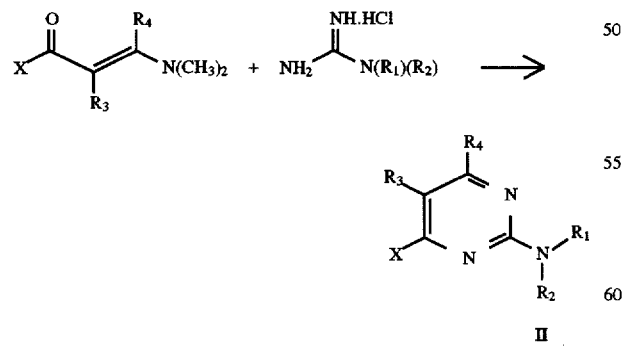

This method provides substituted 2-amino-4-arylpyrimidine compounds of formula II upon reaction of a suitably substituted aryl enamine with an appropriated substituted guanidine hydrochloride.

Method D:

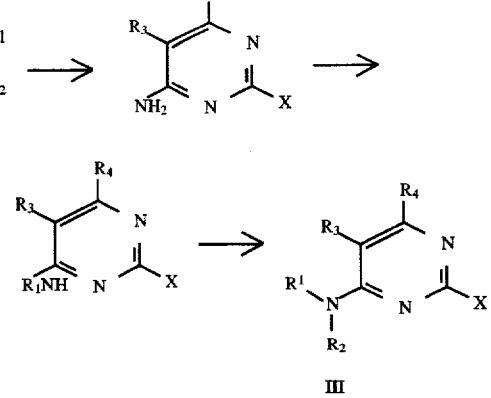

In this method, treatment of a suitable aryl amidine with 3-ethoxyacryonitrile provides a 2-aryl-4-aminopyrimidine compound which, upon condensation with an appropriate ketone under reductive conditions, yields a 2-aryl-4-aminopyrimidine compound (i.e., a secondary amine). Acylation of the secondary amine followed by reduction provides the substituted 2-aryl-4-aminopyrimidine compound of formula III.

Method E:

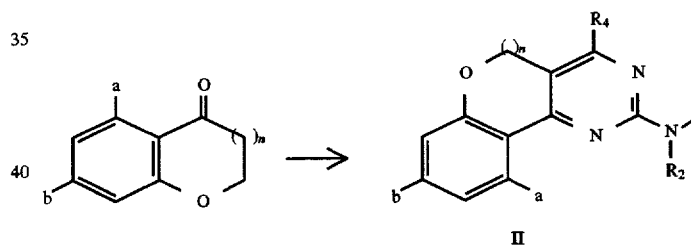

This method provides pyrimidine-containing compounds where a cycloalkyl moiety is fused to the pyrimidine ring at positions 4 and 5. Specifically in this method, an appropriately substituted ketone is condensed with a suitably substituted guanidine derivative to yield a substituted 2-amino-4-arylpyrimidine compound represented by formula II. Substituents a and b on the phenyl ring are as defined above with regard to substituted aryl derivatives.

The triazine-containing compounds of formula IV may be prepared by the reaction scheme of Methods F and G which involve sequential displacement of chloride from cyanuric chloride.

Method F:

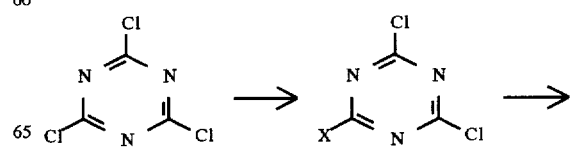

Method F:

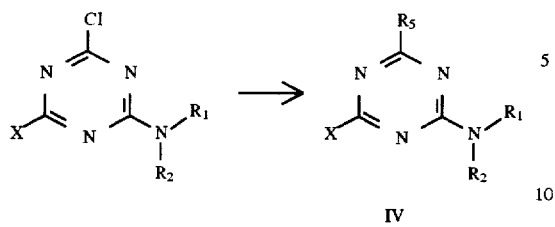

IV

In this method, treatment of cyanuric chloride with a suitable aryl derivative provides an aryl substituted dichlorotriazine. Subsequent reaction with an appropriately substituted amine produces a substituted 2-amino-4-aryl-6-chlorotriazine. Substitution of the 6-chloro substituent yields the triazine compounds of formula IV.

Method G:

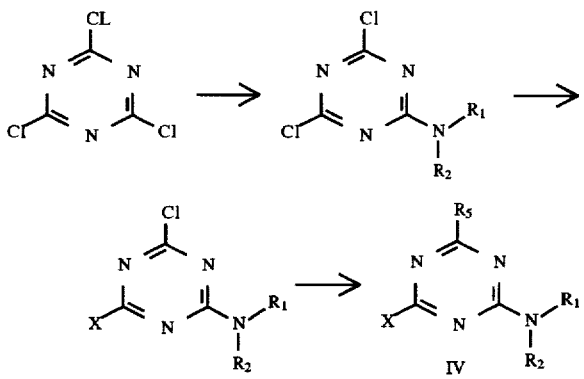

IV

In this method, cyanuric chloride is first treated with an appropriately substituted amine followed by reaction with a suitable aryl derivative to yield a substituted 2-amino-4-aryl-6-chlorotriazine which may then be converted into a triazine compound of formula IV by displacement of the remaining 6-chloro substituent.

The triazole-containing compounds of formula V may be prepared by the reaction scheme of Method H which involves synthesis of a thiourea which is then cyclized to yield the triazole-containing compounds of formula V.

Method H:

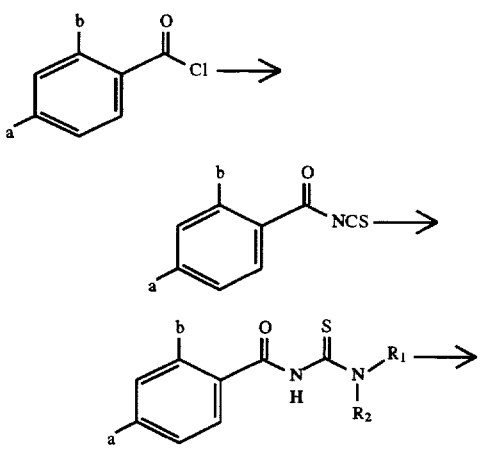

Method H: (continued)

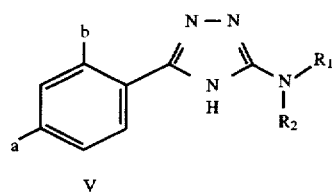

V

In this method, conversion of a benzoyl chloride to the corresponding thiocyanate, followed by reaction with an appropriately substituted amine yields a thiourea. The thiourea may then be converted to the 2-amino-5-aryltriazole compounds of formula V. This reaction scheme may be modified to prepare compounds of formula VI as disclosed in Example 4.

The compounds of the present invention are substituted amino compounds and, as such, are generally utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structures I through VI may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}$I]tyrosine-CFR) to its receptor (e.g. receptors prepared from rat cerebral cortex membranes). The radioligand binding assay described by DeSouza et al. (supra, 1987) provides an assay for determining a compound's affinity for the CRF receptor. Such activity is typically calculated from the IC$_{50}$ as the concentration of a compound necessary to displace 50% of the radiolabeled ligand from the receptor, and is reported as a "K$_i$" value calculated by the following equation:

$$K_i = \frac{IC_{50}}{1 + L/K_D}$$

where L=radioligand and K$_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 µM. In a preferred embodiment of this invention, a CRF receptor antagonist has a $K_i$ of less than 1 µM, and more preferably less than 0.25 µM (i.e., 250 nM). (CRF receptor antagonists of this invention having a $K_i \leq 250$ nM, as well as the experimental methods employed to measure such activity, are presented in Example 7.)

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis., asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structures I through VI) and a pharmaceutically acceptable carrier and/or diluent. The CRF receptor antagonist is present in the composition in an amount which is effective to treat a particular disorder—that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg. to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

The following examples are provided for purposes of illustration, not limitation.

EXAMPLES

The thiadiazole-, pyrimidine-, triazine- and triazole-containing compounds of the present invention may be prepared by the methods disclosed in Examples 1–4. The preparation of representative thiadiazole-containing compounds by Method A are presented in Example 1. The preparation of representative pyrimidine-containing compounds by Methods B through E are presented in Example 2. The preparation of representative triazine-containing compounds by Methods F and G are presented in Example 3. The preparation of representative triazole-containing compounds by Method H are presented in Example 4.

Example 5 identifies the structure and reference number of representative compounds of this invention synthesized by the methods disclosed in Examples 1–4. Example 6 presents the spectral characterization for representative compounds identified in Example 5 and prepared as described in Examples 1–4.

Example 7 presents a method for determining the receptor binding activity ($K_i$), and identifies representative CRF receptor antagonists of this invention having a $K_i \leq 250$ nM. Example 8 discloses an assay for screening compounds of this invention for CRF-stimulated adenylate cyclase activity.

EXAMPLE 1

Synthesis of Thiadiazole-Containing Compounds

In this example, the preparation of the thiadiazole-containing compounds of the present invention is described. The thiadiazole-containing compounds of structural formula I are prepared by reaction of an appropriately substituted amidine with perchloromethyl mercaptan followed by reaction with a suitable amine. This method of preparation is referred to as Method A and is represented schematically below.

Method A:

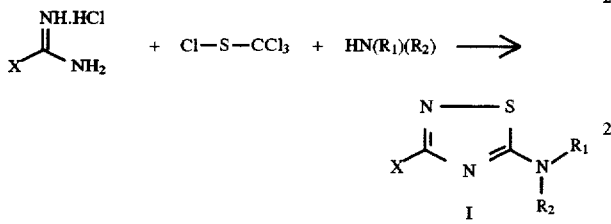

The following two preparations exemplify the synthesis of thiadiazole-containing compounds by Method A.
1. The Synthesis of I-1: 2-(N-dicyclopropylmethyl-N-propylamino)-4-(2',4'-dichlorophenyl)-5-azathiazole.

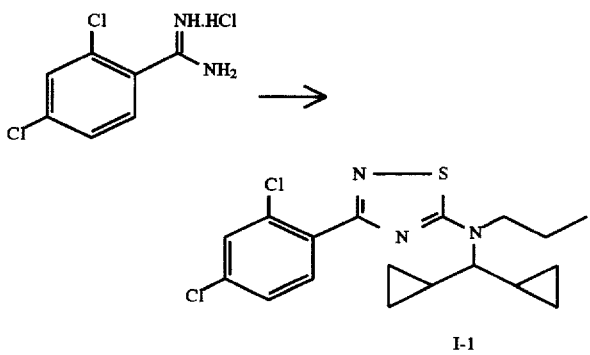

To a solution of 2,4-dichlorobenzonitrile (1.0, 5.8 mmol) in dry toluene (12 mL) was added a 0.67M solution of methyl (amide) aluminum chloride (34.8 mL, 23.2 mmol) in toluene at 25° C. This solution was heated at reflux under nitrogen for 24 hours and the reaction was followed by thin layer chromatography (TLC). The reaction mixture was cooled and the aluminum complex was decomposed by carefully pouring the solution into a slurry of silica gel (50 g) in dichloromethane (400 mL). The mixture was stirred for 1 hour and the silica gel filtered. The filter cake was further washed with 20% methanol/dichloromethane (500 mL). Evaporation of the filtrate yielded the amidine (807 mg, 61%) as a white powder.

To a suspension of the amidine (105 mg, 0.47 mmol) in tetrahydrofuran (5 mL) at 0° C. was added triethylamine (320 mL, 2.33 mmol) followed by perchloromethyl mercaptan (129 mg, 0.69 mmol). Stirring for 2 hours was followed by addition of N-propyl-N-dicyclopropanemethyl amine (107 mg, 0.69 mmol). The resulting cream suspension was then warmed to 50° C. for 48 hours (reaction monitored by TLC). The reaction was then cooled to 25° C. and distributed between diethyl ether (200 mL) and water (100 mL). The organic phase was washed with a saturated solution of sodium bicarbonate (100 mL), dried over magnesium sulfate, filtered and the solvent removed on a rotary evaporator giving crude I1 which was purified by flash column chromatography (silica gel, 10% diethyl ether/hexane) to afford I1 (98 mg, 55%) as a tan oil.
2. The Synthesis of I2: 2-(N-dicyclopropylmethyl-N-propylamino)-4-(2', 4', 6'-trichlorophenyl)-5-azathiazole.

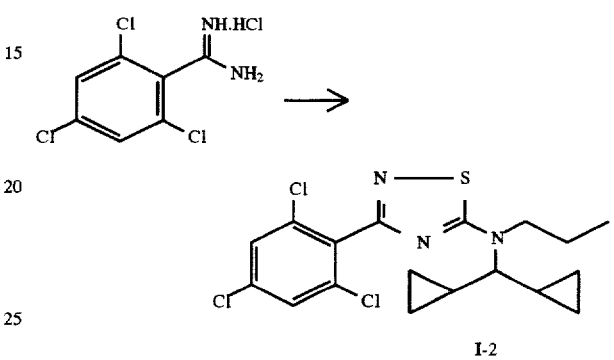

To a solution of 2,4,6-trichlorobenzonitrile (2.5 g, 12.1 mmol) in dry toluene (24 mL) was added a 0.67M solution of methyl (amide) aluminum chloride (75.8 mL, 50.8 mmol) in toluene at 25° C. This solution was heated at reflux under nitrogen for 24 hours (reaction followed by TLC). The reaction mixture was cooled and the aluminum complex was decomposed by carefully pouring the solution into a slurry of silica gel (75 g) in dichloromethane (600 mL). The mixture was stirred for 1 hour and the silica gel filtered. The filter cake was further washed with 20% methanol/dichloromethane (600 mL). Evaporation of the filtrate yielded the requisite amidine (2.26 g, 72%) as a white powder.

To a suspension of the amidine (200 mg, 0.77 mmol) in tetrahydrofuran (8 mL) at 0° C. was added triethylamine (428 mL, 3.08 mmol) followed by perchloromethyl mercaptan (214 mg, 1.15 mmol). Stirring for 2 hours was followed by addition of N-propyldicyclopropanemethyl amine (294 mg, 1.92 mmol). The resulting cream suspension was then warmed to 50° C. for 48 hours (reaction monitored by TLC).

The reaction was then cooled to 25° C. and distributed between diethyl ether (200 mL) and water (100 mL). The organic phase was washed with a saturated solution of sodium bicarbonate (100 mL), dried over magnesium sulfate, filtered and the solvent removed on a rotary evaporator giving crude I-2 which was purified by flash column chromatography (silica gel, 5% diethyl ether/hexane) to afford I-2 (198 mg, 62%) as a tan oil.

EXAMPLE 2

Synthesis of Pyrimidine-Containing Compounds

In this example, the preparation of pyrimidine-containing compounds of the present invention is described. The pyrimidine-containing compounds are prepared by Methods B, C, D, and E as discussed in greater detail below.
Method B:

Method B provides the pyrimidine-containing compounds of the present invention in two steps. In the first step, a 2,4-dichloropyrimidine compound is treated with an appropriately substituted aryl boronic acid to yield a 2-chloro-4-arylpyrimidine compound. Subsequent reaction with a suitable amine produces a substituted 2-amino-4-arylpyrimidine compound of the present invention.

The following schemes more specifically detail the preparation of the pyrimidine-containing compounds of the present invention by Method B.

1. The Synthesis of II-1 through II-9.

| Y | R₃ | R₄ |
|---|----|----|
| Cl | H | H |
| H | Me | H |
| H | H | Me |
| H | F | H |
| H | Cl | H |
| H | H | Cl |

| Y | R₃ | R₄ | | Y | R₃ | R₄ |
|---|----|----|---|----|----|----|
| Cl | H | H | II-1 | Cl | H | H |
| Cl | Me | H | II-2 | Cl | Me | H |
| Cl | H | Me | II-3 | Cl | H | Me |
| Cl | F | H | II-4 | Cl | F | H |
| Cl | Cl | H | II-5 | Cl | Cl | H |
| Cl | H | Cl | II-6 | Cl | H | Cl |
| H | Me | H | II-7 | H | Me | H |
| H | Br | H | II-8 | H | Br | H |
| H | H | H | II-9 | H | H | H |
| Cl | H | * | | | | |

*2,4-dichlorophenyl

Method B provides 2-amino-4-arylpyrimidine compounds II by the following general reaction scheme.

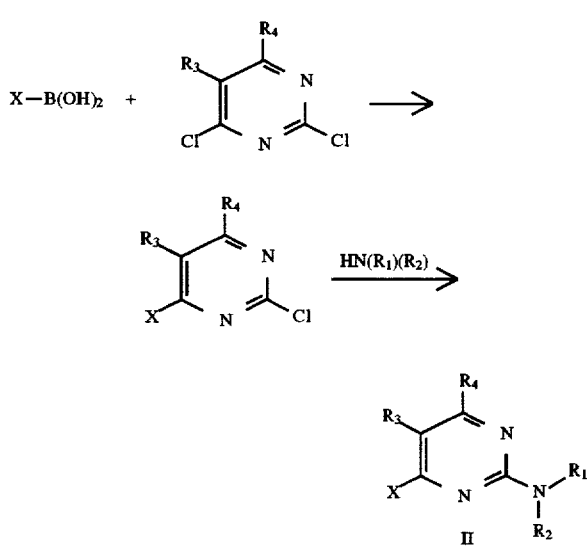

2. General Procedure for the Synthesis of 2-Chloro-4-Arylpyrimidines from Arylboronic Acids and 2,4-Dichloropyrimidines.

A mixture of 2,4-dichloropyrimidines (10 mmol), chlorobenzeneboronic acids (12 mmol), tetrakis(triphenylphosphine)palladium (3–10 mol %), and sodium carbonate (30 mmol) in a solvent system of 8:1:4 benzene/ethanol/water (26 mL) was heated to reflux for 16 to 48 hours and allowed to cool to room temperature. After concentration, the residue was partitioned between ethyl acetate and water (30/30 mL). The separated organic layer was washed with water (2×20 mL) and dried over sodium sulfate. Solvent removal gave the crude products as pale yellow to yellow solids (50–100%) which were either purified by silica gel column chromatography or carried to the next step without further purification.

3. General Procedure for the Synthesis of Substituted 2-Amino-4-Arylpyrimidines (II-1 through II-9).

2-Chloro-4-arylpyrimidines (0.23 mmol) and N-propyl-N-dicyclopropanemethyl amine (1.40 mmol) were mixed and heated at about 120° C. on an oil bath for 1–5 hours. After cooling to room temperature, the reaction mixture was dissolved in dichloromethane (5 mL) and washed with water (2×5 mL). The separated organic layer was dried over sodium sulfate, concentrated to give crude products as yellow to brown oil which were purified by preparative TLC (50–80% yield) with ethyl acetate/hexane solvent system.

The following pyrimidine was formed when the above general reaction was carried out with N-propyl-N-cyclopropylmethyl amine instead of N-propyl-N-dicyclopropylmethyl amine at about 120° C. for 2 hours.

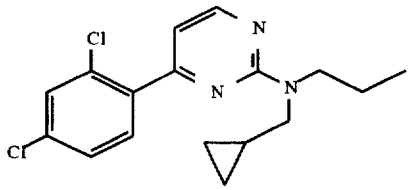

4. The Synthesis of II-10: 2-(N-dicyclopropylmethyl-N-propyl)-4-(2',4'-dichlorophenyl)-5-acetamidopyrimidine.

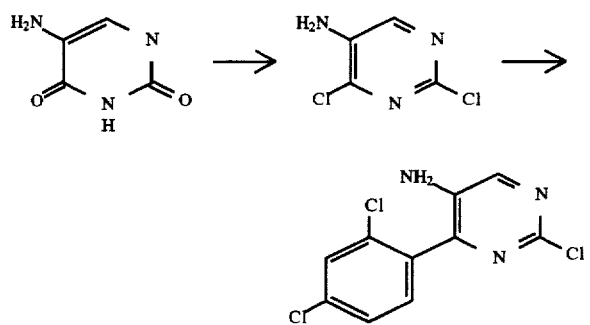

A mixture of 5-aminouracil (5.0 g, 39 mmol) and N,N-dimethylaniline (7.2 g, 59 mmol) in 20 mL of phosphorus oxychloride was heated under reflux for 17 hours. After removal of phosphorous oxychloride under reduced pressure, ice water (40 mL) was added to the residue with stirring. The aqueous solution was extracted with ethyl acetate (3×30 mL), and the combined organic extracts were washed with water (40 mL), dried over sodium sulfate. Solvent removal gave the 2,4-dichloro-5-aminopyrimidine as yellow solid (0.72 g, 11%) which was used without further purification.

For the coupling reaction of the pyrimidine to dichlorobenzene boronic acid, see the general procedure described above.

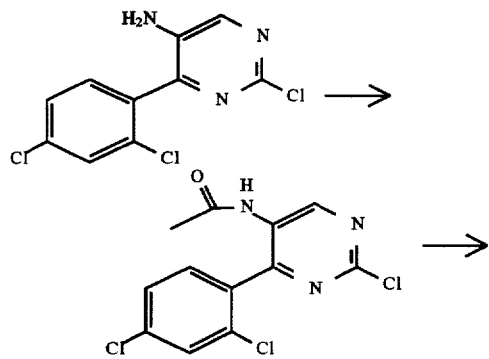

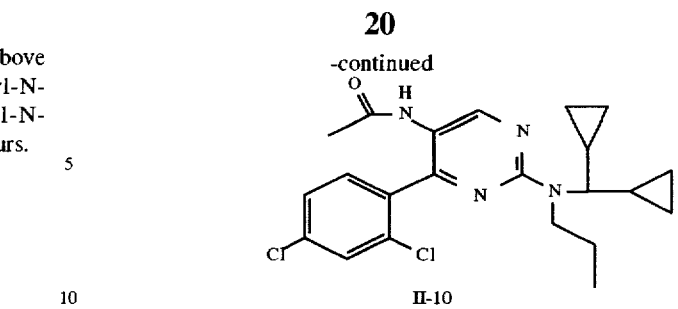

A solution of the coupled product (10 mg) and acetic anhydride (1 ml) was heated at 100° C. for 1 hour. The reaction was cooled and blown to a residue with a stream of dry nitrogen. The residue was taken up in N-dicyclopropylmethyl-N-propylamine (100 mg) and heated at 120° C. for 10 hours. The resulting solution was then cooled to room temperature and purified by preparative chromatography on two 20×20 cm silica gel plates 0.5 mm thick, eluting with 20% ethyl acetate in hexanes. After extraction, II-10 (2.3 mg) solidified upon standing.

Method B may also be used to prepare pyrimidine-containing compounds of formula III. The following scheme is representative of the preparation of pyrimidines of formula III by Method B.

The Synthesis of III-1: 2-(2',4'-dichlorophenyl)-4-(N-dicyclopropylmethyl-N-propylamino)pyrimidine.

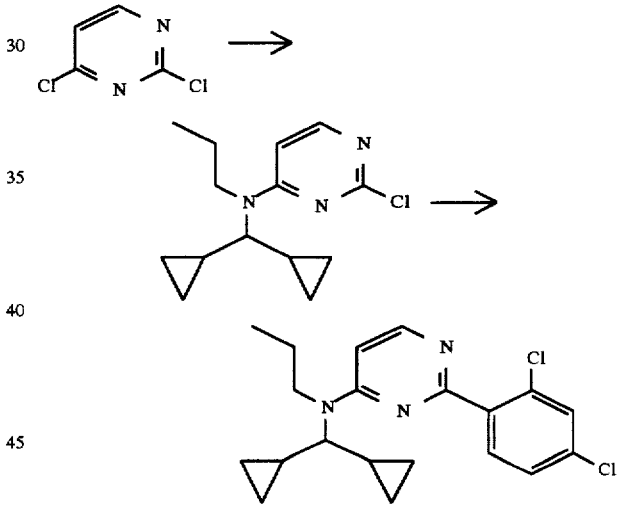

A solution of 2,4-dichloropyrimidine (300 mg, 2.01 mmol) and N-propyl-N-dicyclopropylmethyl amine (400 mg, 2.61 mmol) in 5 ml anhydrous dioxane was heated at reflux for 16 hours. The reaction was cooled to room temperature and the solvent was removed under vacuum. The residue was dissolved in 250 ml ethyl acetate, washed with 1M aqueous hydrochloric acid (3×30 ml), saturated aqueous sodium bicarbonate (2×30 ml) and distilled water (2×30 ml). The aqueous solution was back extracted with ethyl acetate (2×30 ml). The combined organic layers was dried over sodium sulfate, filtered and concentrated. Flash chromatography (20% ethyl acetate/hexanes) gave pure 2-chloro-4-(N-propyl-N-dicyclopropyl-methyl) aminopyrimidine (300 mg, 56%).

A mixture of 2-chloro-4-(N-propyl-N-dicyclopropylmethyl)-aminopyrimidine (45 mg, 0.17 mmol), 2,4-dichlorobenzeneboronic acid (43 mg, 0.23 mmol) and tetrakis(triphenylphosphine)palladium (20 mg, 0.02 mmol) in toluene (2 ml), sodium carbonate (3 ml) and ethanol (1 ml) was heated under reflux for 2 days. The reaction mixture was cooled to room temperature, water (10 ml) was added, and the toluene layer was separated. The aqueous layer was extracted with ethyl acetate and the combined organic layers was dried over sodium sulfate, filtered and evaporated. The product was purified by preparative TLC (20% ethyl acetate/hexanes), yielding 43 mg III-1 (67%).

Method C:

The pyrimidines of the present invention may also be prepared by Method C. Method C provides the pyrimidine-containing compounds by reaction of a suitably substituted aryl enamine with an appropriately substituted guanidine hydrochloride. Method C provides 2-amino-4-arylpyrimidine compounds by the following general reaction scheme.

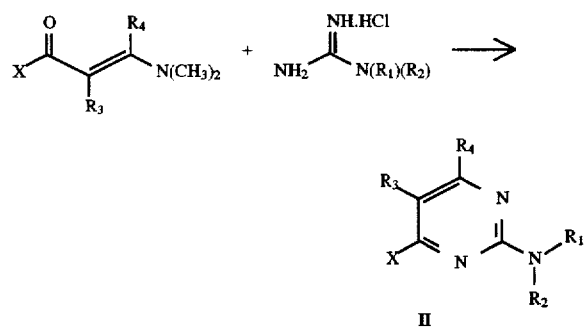

The following schemes more specifically detail the preparations of the pyrimidine-containing compounds of the present invention by Method C.

1. The Synthesis of II-11: 2-(N-dicyclopropylmethyl-N-propylamino)-4-(2',4',6'-trichlorophenyl)-pyrimidine.

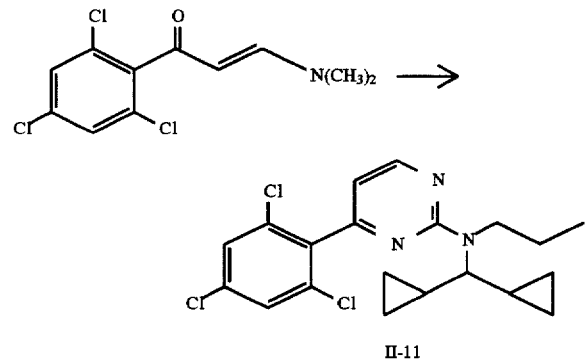

II-11

A solution of 2,4,6-trichloroacetophenone (285 mg, 1.28 mmol) in dimethylformamide dimethylacetal (1 mL) was heated at 90° C. under an argon atmosphere. The progress of the reaction was monitored by TLC (ethyl acetate:ethanol 9:1). After 15 hours, the reaction was cooled in an ice bath and a small amount of dark solid was removed by filtration and washed with hexane (1 mL). The filtrate was evaporated in vacuo providing the intermediate enamine as a homogeneous solid by TLC after drying under vacuum (240 mg, 67%). MS (ion spray): 278 (M+H).

A solution of a portion of the enamine (28 mg, 0.1 mmol) and $N^1$-dicyclopropylmethyl-$N^1$-propyl guanidine hydrochloride (23 mg, 0.1 mmol) in 0.1 Methanolic sodium ethoxide (1 mL, 0.1 mmol) was heated at reflux under a nitrogen atmosphere. The progress of the reaction was monitored by TLC (hexane:ether 5:1 and ethyl acetate:ethanol 9:1). After 20 hours, the reaction was cooled to ambient temperature and purified by preparative thin layer chromatography (silica gel) using hexane:ether (5:1). The major fast moving band ($R_f$=0.69) was eluted with hot ethanol and the silica gel was removed by filtration. Evaporation of the filtrate provided the II-11 (5.3 mg).

2. The Synthesis of II-12: 2-(N-dicyclopropylmethyl-N-propylamino)-4-(2'4'-dichlorophenyl-5-(dimethylcarboxamido)pyrimidine.

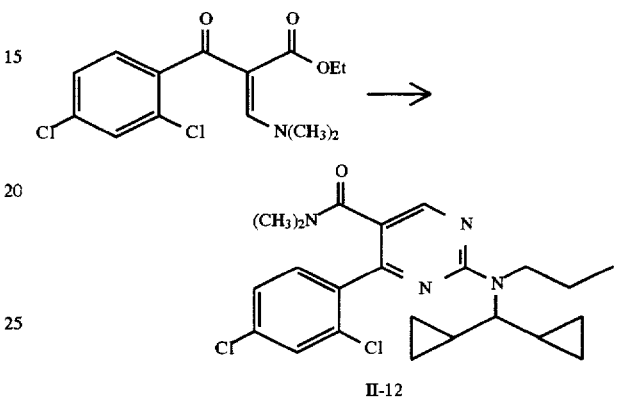

II-12

A solution of ethyl (2,4-dichlorobenzoyl) acetate (800 mg, 3 mmol) in dimethyl formamide dimethyl acetal (0.7 mL, 5 mmol) and dimethylformamide (1 mL) was stirred at ambient temperature. The progress of the reaction was monitored by TLC (ethyl acetate: hexane 1:5) and after 16 hours the yellow reaction solution was diluted with ether (50 mL) and washed with water (25 mL). The ether layer was dried over magnesium sulfate and evaporated in vacuo. The resulting yellow crystalline solid (1.5 gm) of enamine was used directly in the next step. MS (ion spray): 316 (M+H).

The enamine (420 mg, 1.33 mmol) and $N^1$-dicyclopropylmethyl-$N^1$-propyl guanidine hydrochloride (310 mg, 1.33 mmol) were combined with 0.1M ethanolic sodium ethoxide (13.3 mL, 1.33 mmol) and heated at reflux for 16 hours. The reaction was partioned between methylene chloride and brine and the organic layer was dried over sodium sulfate and evaporated to an oil. Purification by flash chromatography (silica gel, methylene chloride) provided the ethyl ester pyrimidine intermediate as a colorless oil (200 mu) after evaporation of fractions 1–3 (100 ml total elutant) from the column. MS (ion spray): 448 (M+H).

A portion of the above ethyl ester (100 mg, 0.22 mmol) and potassium cyanide (2 mg) were placed in a tube and dimethylamine gas (ca. 2 ml) was condensed into the tube. The tube was sealed and the reaction solution was stirred at ambient temperature for 16 hours. The dimethyl amine was allowed to evaporate after the seal was broken and the residue was partioned between ethyl acetate and water. The organic layer was dried over magnesium sulfate and evaporated in vacuo. Purification of the residue by flash chromatography (methylene chloride followed by methylene chloride:methanol 95:5) gave 28 mg of II-12 which was further purified by preparative TLC (methylene chloride:methanol 95:5) ($R_f$=0.3) providing 11.8 mg II-12.

3. The Synthesis of II-13: 2-(N-dicyclopropylmethyl-N-propyl)-4-(2',4'-dichlorophenyl)-5-methylsulfonylpyrimidine.

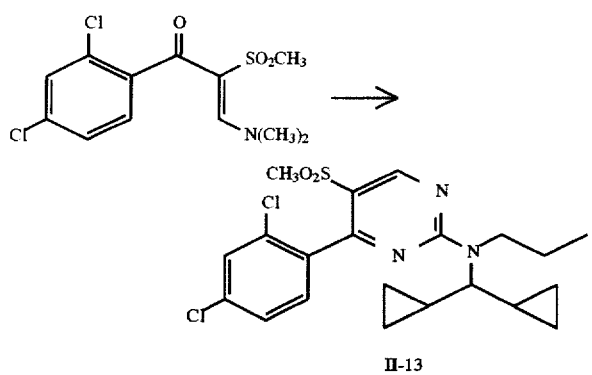

II-13 a. 2,4-Dichlorobenzoic Acid Ethyl Ester.

To a stirring anhydrous ethanol (110 g, 2.390 mol) was dropwise added 2,4-dichlorobenzoyl chloride (50 g, 239 mmol). The solution was allowed to stir at room temperature for overnight. Removal of the solvent gave 52.6 g of ethyl ester as a pale yellow solid. $^1$H NMR (CDCl$_3$): 1.40 (t, 3H), 4.40 (m, 2H), 7.30 (d, 1H), 7.48 (s, 1H), 7.79 (d, 1H).

b. 3-Methylsulfinyl-(2',4'-dichloro)acetophenone.

To a stirring solution of 2,4-dichlorobenzoic acid ethyl ester (40 g, 183 mmol) in anhydrous dimethyl sulfoxide (120 mL) was added potassium t-butoxide (1M solution in t-butyl alcohol) (188 mL, 188 mmol). The mixture was allowed to stir under nitrogen at room temperature for 3 hours. Concentration of the reaction mixture at reduced pressure (water bath, 60° C.–70° C.) yielded a dark brown oil which was dissolved in 200 mL cold water. The aqueous solution was extracted with ether (100 mL×3), then acidified to pH 2–3 by careful addition of conc. Hydrochloric acid, quickly extracted with dichloromethane (100 mL×2). The combined extracts were washed with aqueous sodium bicarbonate (100 mL) and brine (100 mL), dried over magnesium sulfate, and filtered. Removal of the solvent at reduced pressure gave 31g (123 mmol, 67%) of the β-sulfoxide as an orange oil. $^1$H NMR (CDCl$_3$): 2.79 (s, 3H), 4.40 (s, 2H), 7.38 (d, 1H), 7.47 (s, 1H), 7.66 (d, 1H).

c. 3-Methylsulfonyl-(2',4'-dichloro)acetophenone.

To a stirring solution of the sulfoxide (0.51 g, 2.0 mmol) in anhydrous methylene chloride (6 mL) in ice water bath was added a solution of m-chloroperoxybenzoic acid (700 mg, 2.4 mmol) in methylene chloride (2 mL) under nitrogen. The mixture was allowed to stir at room temperature for 1 hour. The reaction mixture was washed with 1M aqueous sodium thiosulfate (50 mL×3) aqueous sodium bicarbonate (50 mL) and brine (50 mL), dried over magnesium sulfate, and filtered. Removal of the solvent at reduced pressure gave 0.55 g of the sulfone as a yellow solid. $^1$H NMR (CDCl$_3$): 3.19 (s, 3H), 4.64 (s, 2H), 7.40 (d, 1H), 7.50 (s, 1H), 7.66 (d, 1H). Mass (ion spray): 267, 269 (M+H).

d. 1-(2',4'-Dichloro)benzoyl-1-methylsulfonyl-2-(NN-dimethylamino)ethene.

To a stirring solution of the sulfone (0.55g, 2.0 mmol) in toluene (4 mL) was added N,N-dimethylformamide dimethyl acetal (635 mg, 5.0 mmol). The mixture was refluxed for 1 hour. The reaction mixture was concentrated and chromatographed over a silica gel column, eluting with 5% methanol in dichloromethane The product-containing fractions were combined and concentrated to yield 0.48 g (74%) of the dimethylamino ethene as a brown oil. $^1$H NMR (CDCl$_3$): 2.82 (m, 3H), 3.0 (s, 3H), 3.29 (m, 3H), 7.30 (d, 1H), 7.41"7.45 (m, 2H), 7.85 (s, 1H). Mass (ion spray): 321, 323, 326 (M+H).

e. II-13: 2-(-dicyclopropylmethyl-N-propylamino)-4-(2',4'-dichlorophenyl)-5-methylsulfonylpyrimidine.

To a stirring solution of the dimethylamino ethene (62 mg, 0.19 mmol) in aqueous methanol (water 0.1 mL, methanol 1 mL) was added N$^1$-dicyclopropylmethyl-N$^1$-propyl guanidine hydrochloride (45 mg, 0.19 mmol) and sodium carbonate (14 mg, 0.13 mmol). The mixture was refluxed for 4 hours. The reaction mixture was concentrated and chromatographed over a silica gel column, eluting with 5% methanol in dichloromethane. The product-containing fractions were combined and concentrated to yield 24 mg (28%) of II-13 as a white solid.

4. The Synthesis of II-14: 2-(N-dicyclopropylmethyl-N-propylamino)-4-(2',4'-dichlorophenyl)-5-methylsulfinylpyrimidine.

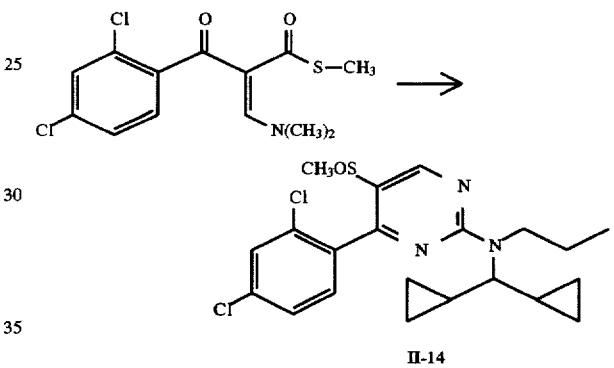

II-14 a. 1-(2',4'-Dichloro)benzoyl-1-methyisulfinyl-2-(N,N,-dimethylamino)ethene.

To a stirring solution of the sulfoxide (prepared as described in the synthesis of II-13) (1.0 g, 3.98 mmol) in toluene (8 mL) was added N,N-dimethylformamide dimethyl acetal (1.14 g, 9.56 mmol). The mixture was refluxed for 1 hour. The reaction mixture was concentrated and chromatographed over a silica gel column, eluting with 5% methanol in dichloromethane. The product-containing fractions were combined and concentrated to yield 0.92 g (76%) of the dimethylamino ethene as a brown oil. $^1$H NMR (CDCl$_3$): 2.72 (m, 3H), 3.23 (m, 6H), 7.30 (d, 1H), 7.32 (s, 2H), 7.43 (s, 1H), 7.46 (s, 1H). Mass (ion spray): 306, 308 (M+H).

b. II-14: 2-(N-dicyclopropylmethyl-N-propylamino)-4-(2',4'-dichlorophenyl)-5-methylsulfinylpyrimidine.

To a stirring solution of the dimethylamino ethene (92 mg, 0.30 mmol) aqueous methanol (water 0.15 mL, methanol 1.5 mL) was added N$^1$-dicyclopropylmethyl-N$^1$-propyl guanidine hydrochloride (70 mg, 0.30 mmol) and sodium carbonate (22 mg, 0.21 mmol). The mixture was refluxed for 4 hours. The reaction mixture was concentrated and chromatographed over a silica gel column, eluting with 5% methanol in dichloromethane The product-containing fractions were combined and concentrated to yield 15 mg (11%) of II-14 as a colorless oil.

5. The Synthesis of II-15: 2-(N-dicyclopropylmethyl-N-propyl)-4-(2',4'-dichlorophenyl-5-ethylpyrimidine.

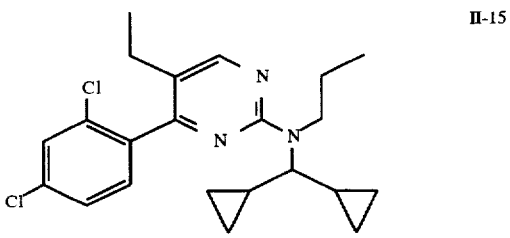

II-15

To a solution of 2,4-dichlorobenzoyl chloride (4.5 g, 21.5 mmol) in tetrahydrofuran (30 ml) was treated with copper (I) iodide (200 mg) and cooled to −20° C. Propyl magnesium bromide (2.0M in diethyl ether, 11 ml, 11 mmol) was slowly injected (10 minutes) under nitrogen. The yellow suspension was stirred at −20° C. to −15° C. for 10 minutes, the cooling bath was removed and stirring was continued for another hour. The reaction was quenched with water, and the product was extracted with toluene. The organic phase was washed with 1N aqueous hydrochloric acid, bicarbonate and brine, filtrated through a silica gel pad and concentrated in vacuo to give 2,4-dichlorobutyrophenone as a yellowish oil (4.5 g, 96%) which was used in the next step without further purification. $^1$H NMR (CDCl$_3$): 0.99 (t, 3H), 1.74 (m, 2H), 2.91 (t, 2H), 7.32 (d, 1H), 7.42 (d, 1H), 7.44 (s, 1H).

2',4'-Dichlorobutyrophenone (65 mg, 0.3 mmol) and, N,N-dimethylformamide dimethyl acetal (45 ml, 0.3 mmol) were mixed in a sealed reaction-vial and heated to 95° C. for 12 hours. The resulting brown oil was treated with N$^1$-dicyclopropylmethyl-N$^1$-propyl guanidine hydrochloride salt (23 mg, 0.1 mmol) and the mixture was heated to 160° C. for 2 hours. The crude mixture was purified on a preparative TLC plate with 1:10 ethyl acetate-hexanes to give II-1 as a colorless oil.

6. The Synthesis of II-6: 2-(N-dicyclopropylmethyl-N-propylamino)-4-(4'-bromophenyl)-5-methylpyrimidine.

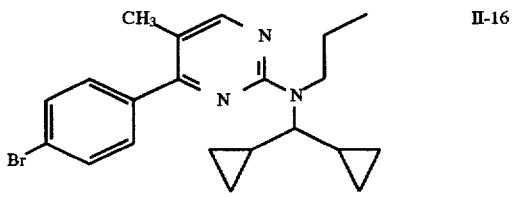

II-16

A mixture of 4'-bromopropiophenone (2.15 g, 10 mmol) and N,N-dimethylformamide dimethyl acetal (1.65 ml, 12 mmol) was heated to reflux overnight under nitrogen which gave the enamine and methyl 4'-bromobenzoate with about 1:1 ratio. Chromatography on silica gel with 1:5 ethyl acetate-hexanes first eluted the methyl ester, and the enamine was eluted with ethyl acetate. $^1$H NMR (CDCl$_3$): 2.14 (s, 3H), 3.08 (s, 6H), 6.85 (s, 1H), 7.31 (d, 2H), 7.51 (s, 2H).

A solution of the enamine (200 mg, 0.88 mmol) and N$^1$-cyclopropyl-N$^1$-propyl guanidine hydrochloride (90 mg, 0.47 mmol) in ethanol (5 ml) was refluxed under nitrogen for 24 hours. Ethanol was evaporated in vacuo and the residue was chromatographed on silica gel column with 1:5 ethyl acetate-hexanes to give the II-16 as a colorless oil (25 mg).

7. The Synthesis of II-17 through II-21.

Pyrimidines II-17 through II-21 are prepared by Method C starting with the appropriately substituted aryl ketone. The following is a general procedure for the preparation of these pyrimidines starting with the appropriate ketone. These pyrimidines are prepared from 4-methoxyacetophenone, 4-iodoacetophenone, 3,4-dichloropropiophenone, 2,4-dimethoxyacetophenone, and 2,3,4-trichloroacetophenone, respectively.

A mixture of the ketone (0.33 mmol) and N,N-dimethylformamide (45 ml, 0.34 mmol) was heated to 100° C. for 12 hours. N$^1$-dicyclopropylmethyl-N$^1$-propyl guanidine hydrochloride salt (23 mg, 0.1 mmol) was added followed by ethylene glycol (0.1 ml). The mixture was heated to 160° C. for 2 hours and cooled down to room temperature. The crude product was loaded directly to a preparative TLC plate and chromatographed with 1:10 or 1:5 ethyl acetate -hexanes to give the product.

The pyrimidine-containing compounds were isolated as: II-17, colorless oil; II-18, colorless oil; II-19, colorless oil; II-20 white solid; II-21, colorless oil.

8. The Synthesis of II-22: 2-(N-dicyclopropylmethyl-N-propylamino)-4-(2',4',6'-trimethoxyphenyl )pyrimidine.

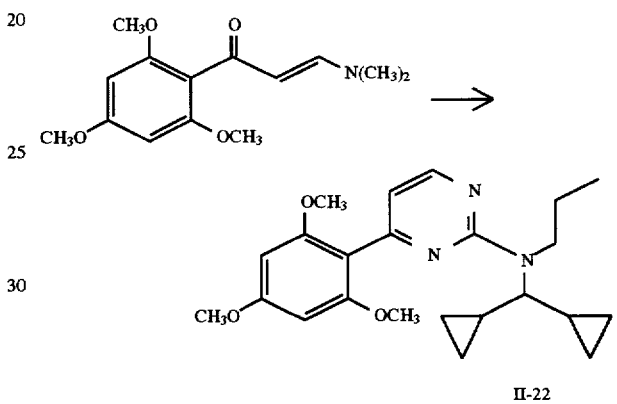

II-22

2,4,6-Trimethoxyacetophenone (1.0 g, 4.76 mmol) was dissolved in 4 ml anhydrous dimethylformamide. To this solution, N,N-dimethylformamide dimethyl acetal (2.30 g, 19.30 mmol) was added at room temperature under nitrogen. The resulting solution was then heated at reflux for 16 hours. The reaction solution was diluted with ethyl acetate (250 ml), washed with distilled water (3×30 ml). The aqueous solution was back extracted with dichloromethane (3×50 ml). The combined organic layers was dried over anhydrous sodium sulfate, filtered and evaporated. Flash chromatography on silica gel (5% methanol in ethyl acetate) gave the enaminone (0.94 g, 75%) as white solid. $^1$H NMR (CDCl$_3$): 2.81 (s, 3H), 2.96 (s, 3H), 3.74 (s, 6H), 3.80 (s, 3H), 5.30 (d, 1H), 6.11 (s, 2H), 7.20 (broad, 1H). Mass (ion spray): 266 (M+H), 288 (M+Na).

A suspension of N$^1$-propyl-N$^1$-dicyclopropylmethyl guanidine hydrochloride (68 mg, 0.30 mmol) and potassium t-butoxide (34 mg, 0.30 mmol) in methanol was stirred at room temperature under nitrogen for 10 minutes. To this solution, the enaminone (60 mg, 0.23 mmol) was added, and the resulting solution was heated at reflux for 15 hours. Solvent was evaporated under vacuum. The residue was dissolved in 10 ml ethyl acetate and washed with 1M aqueous hydrochloric acid (2×4 ml) and distilled water (2×4 ml). The organic layer was dried over sodium sulfate, filtered and evaporated. Purification by preparative TLC (1% methanol in dichloromethane) gave II-22 (52 mg, 58%).

9. The Synthesis of II-23: 2-(N-dicyclopropylmethyl-N-propyl)-4-(2',6'-dimethoxyphenyl)pyrimidine.

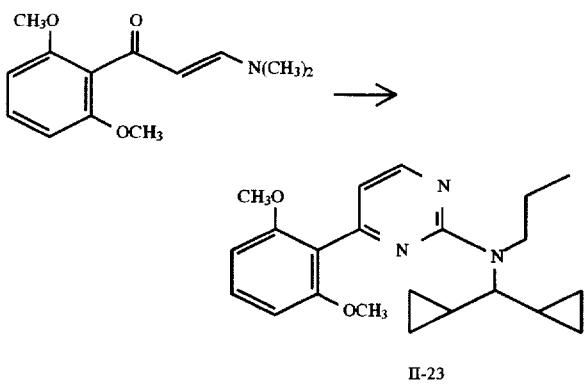

II-23

2,6-Dimethoxyacetophenone (1.02 g, 5.66 mmol) was dissolved in 5 ml anhydrous dimethylformamide. To this solution, N,N-dimethylformamide dimethyl acetal (3.10 g, 26.02 mmol) was added at room temperature under nitrogen. The resulting solution was then heated at reflux for 2 days. The reaction solution was diluted with ethyl acetate (250 ml), and washed with distilled water (3×30 ml). The aqueous solution was back extracted with dichloromethane (4×100 ml). The combined organic layers was dried over anhydrous dichloromethane, filtered and evaporated. The enaminone crystallized and was washed with hexanes and dried (1.26 g, 95%). The product was used in the next step without further purification. $^1$H NMR (CDCl$_3$): 2.80 (s, 3H), 2.94 (s, 3H), 3.73 (s, 6H), 5.28 (d, 1H), 6.53 (d, 2H), 7.18 (t, 1H), 7.20 (broad, 1H). Mass (ion spray): 236 (M+H), 258 (M+H).

A suspension of N$^1$-propyl-N$^1$-dicyclopropylmethyl guanidine hydrochloride (102 mg, 0.44 mmol) and potassium t-butoxide (50 mg, 0.44 mmol) in methanol was stirred at room temperature under nitrogen for 10 minutes. To this solution, the enaminone (80 mg, 0.34 mmol) was added. The resulting solution was then heated to reflux for 20 hours. Solvent was evaporated under vacuum. The residue was dissolved in 8 ml dichloromethane and washed with 1M aqueous hydrochloric acid (2×2 ml) and distilled water (2×2 ml). The organic layer was dried over sodium sulfate, filtered and evaporated. Purification by preparative TLC (1% methanol in dichloromethane) gave II-23 (70 mg, 56%).

10. The Synthesis of II-24: 2-(N-dicyclopropylmethyl-N-propyl)-4-(2',4',6'-trimethylphenyl)pyrimidine.

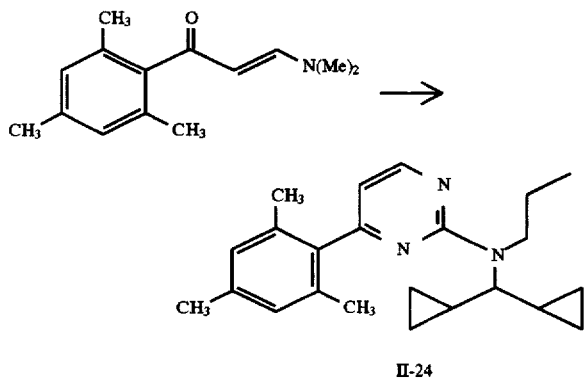

II-24

2,4,6-Trimethylacetophenone (1.05 g, 6.47 mmol) was dissolved in 5 ml anhydrous dimethylformamide. To this solution, N,N-dimethylformamide dimethyl acetal (3.10 g, 26.01 mmol) was added at room temperature under nitrogen. The resulting solution was then heated at reflux for 2 days. The reaction solution was diluted with ethyl acetate (250 ml), washed with distilled water (3×30 ml). The aqueous solution was back extracted with dichloromethane (2×30 ml). The combined organic layers was dried over anhydrous sodium sulfate, filtered and evaporated to give the enaminone as an oil (1.20 g, 86%). $^1$H NMR (CDCl$_3$): 2.19(s, 6H), 2.24 (s, 3H), 2.80 (s, 3H), 2.94 (s, 3H), 5.26 (d, 1H), 6.70 (broad, 1H), 6.80 (s, 2H). Mass (ion spray): 218 (M+H), 218 (M+Na).

A suspension of N$^1$-propyl-N$^1$-dicyclopropylmethyl guanidine hydrochloride (97 mg, 0.42 mmol) and potassium t-butoxide (48 mg, 0.43 mmol) in methanol was stirred at room temperature under nitrogen for 10 minutes. To this solution, the enaminone (70 mg, 0.32 mmol) was added. The resulting solution was then heated at reflux for 20 hours. Solvent was evaporated under vacuum. The residue was dissolved in 6 ml dichloromethane and washed with 1M aqueous hydrochloric acid (2×2 ml), distilled water (2×2 ml). The organic layer was dried over sodium sulfate, filtered and evaporated. Purification by preparative TLC (1% methanol in dichloromethane) gave II-24 (58 mg, 52%).

11. The Synthesis of II-25: 2-N-dicycloropylmethyl-N-propyl)-4-(2', 4', 6'-trimethoxyphenyl)-5-methylpyrimidine.

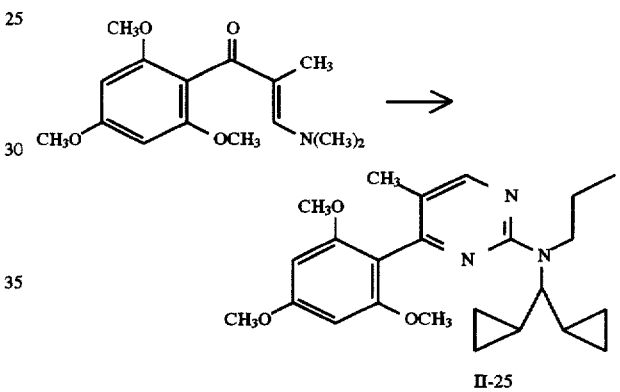

II-25

A mixture of 1,3,5-trimethoxybenzene (1.00 g, 5.95 mmol) and propionyl chloride (0.605 g, 6.54 mmol) in 8 ml 1,2-dichloroethane was cooled in an ice bath under nitrogen and treated portionwise with aluminum trichloride (0.872 g, 6.54 mmol) The reaction mixture was stirred for half an hour at 0° C. and then for 16 hours at room temperature. The reaction solution was diluted with 250 ml dichloromethane, then washed with 1M aqueous hydrochloric acid (2×50 ml), saturated sodium bicarbonate (50 ml), and distilled water (2×50 ml). The aqueous solution was then back extracted with dichloromethane (2×50 ml). The combined organic layers was dried over sodium sulfate, filtered and evaporated. The propiophenone was crystallized from 5:1 ethyl acetate/hexanes and washed with hexanes (0.90g, 70%). $^1$H NMR (CDCl$_3$): 1.14 (t, 3H), 2.75 (q, 2H), 3.78 (s, 6H), (s, 3H), 6.11 (s, 2H). Mass (ion spray): 225 (M+H), 247 (M+Na).

2,4,6-Trimethoxypropiophenone (0.50 g, 2.23 mmol) was dissolved in 3 ml anhydrous dimethylformamide. To this solution, N,N-dimethylformamide dimethyl acetal (1.06 g, 8.90 mmol) was added at room temperature under nitrogen. The resulting solution was then heated at reflux for 1 day. The reaction solution was diluted with ethyl acetate (250 ml) and washed with distilled water (3×50 ml). The aqueous solution was back extracted with ethyl acetate (2×50 ml). The combined organic layers was dried over anhydrous sodium sulfate, filtered and evaporated to oil residue. The enaminone (420 mg, 68%) was crystallized and washed with hexanes and cold ethyl acetate. $^1$H NMR (CDCl$_3$): 2.13 (s, 31H), 3.03 (s, 6H), 3.74 (s, 6H), 3.83 (s, 3H) 6.12 (s, 2H), 6.87 (broad, 1H). Mass (ion spray): 280 (M+H), 302 (M+Na).

A suspension of N-propyl-N-dicyclopropylmethyl guanidine monohydrochloride (19 mg, 0.082 mmol) and potassium t-butoxide (10 mg, 0.089 mmol) in methanol was stirred at room temperature under nitrogen for 10 minutes. To this solution, the enaminone (20 mg, 0.072 mmol) was added. The resulting solution was then heated at reflux for 20 hours. Solvent was evaporated under vacuum. The residue was dissolved in 4 ml ethyl acetate and washed with 1M aqueous hydrochloric acid (2×2 ml), and distilled water (2×2 ml). The organic layer was dried over sodium sulfate, filtered and evaporated. Purification by preparative TLC (1% methanol in dichloromethane) gave II-25 (22 mg, 75%).

12. The Synthesis of II-26: 4-(2',4'-dimethylphenyl)-2-(N-dicyclopropylmethyl-N-propylamino) pyrimidine.

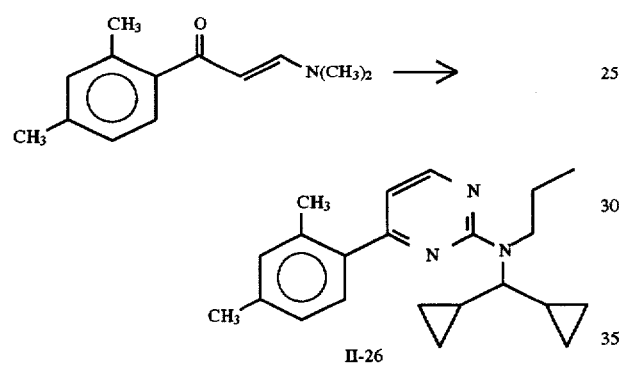

A solution of 2',4'-dimethylacetophenone (30 mg, 0.2 mmole) in 26 microliters of N,N-dimethylformamide dimethylacetal was heated to 80° C. in a sealed tube for 5 hours. This solution was allowed to cool and N-dicyclopropylmethyl-N-propyl guanidine (23 mg, 0.1 mmole) and 0.1 mL ethylene glycol were added. This was stirred and heated to 160° C. for 2 hours. This was allowed to cool to room temperature and poured into ether/water. The organic phase was washed with water, 0.1M aqueous hydrochloric acid and brine, dried over magnesium sulfate and concentrated. The residue was purified by preparative TLC (20% diethyl ether/hexane) to give II-26.

Method D:

Method D provides the pyrimidine-containing compounds (formula III) of the present invention in four steps. A suitable aryl amidine is converted to a 2-amino-4-arylpyrimidine compound by treatment with 3-ethoxyacrytonitrile under basic conditions. Reductive amination of a ketone (e.g., dicyclopropyl ketone) with the 2-aminopyrimidine compound provides a secondary 2-amino-pyrimidine compound which is then acylated with an acid halide (e.g. propionyl chloride) to yield a 2-amido-4-arylpyrimidine compound. Reduction of the amide produces a substituted 2-amino-4-arylpyrimidine compound of the present invention.

Method D is represented schematically by the following general reaction scheme.

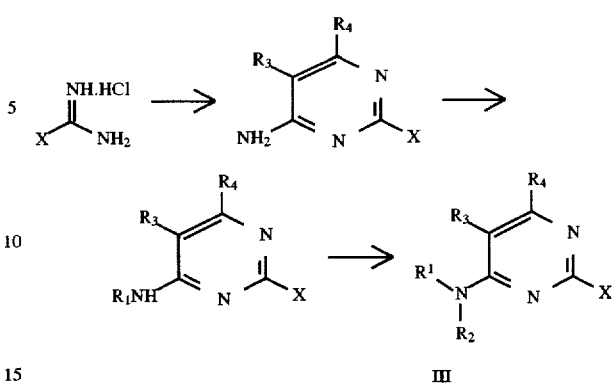

The following scheme more specifically details the preparation of a pyrimidine-containing compound of the present invention by Method D.

1. The Synthesis of II-2: 2-(2',4',6'-trichlorophenyl)-4-(N-dicyclopropylmethyl-N-propylamino)pyrimidine.

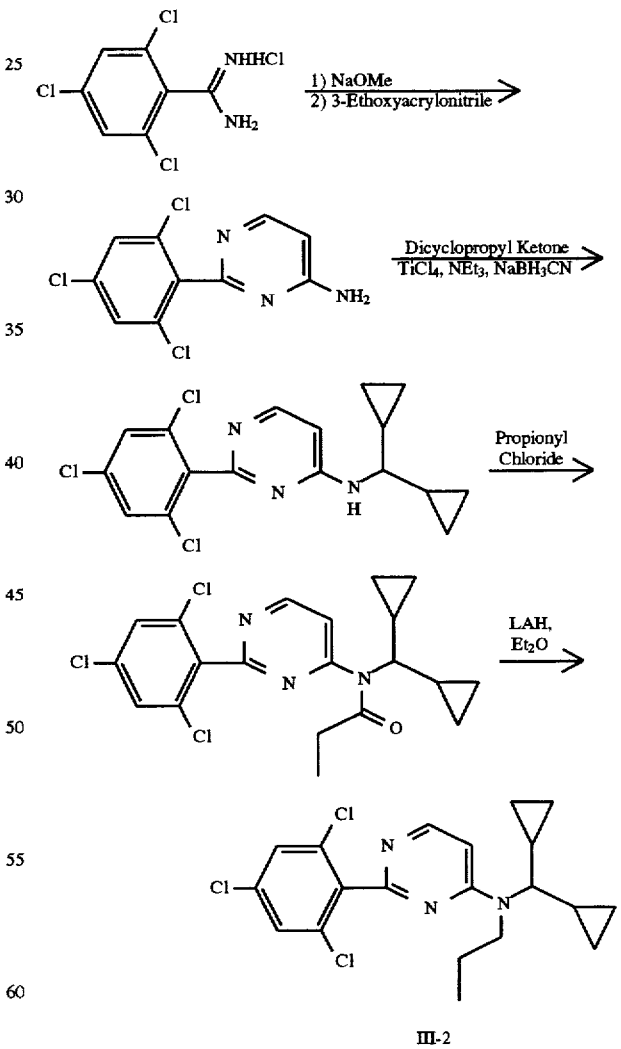

A mixture solution of 2,4,6-trichlorobenzeneamidine monohydrochloride (500 mg, 1.925 mmol) and sodium methoxide (104 mg, 1.925 mmol) in 5 ml of 1:1 methanol/ethylene glycol solvent was stirred at room temperature under nitrogen for 10 minutes. To this solution, 3-ethoxyacrylonitrile (225 mg, 2.317 mmol) was added. The resulting solution was then heated at reflux for 48 hours. Methanol was removed under vacuum. The residue was diluted with 250 ml ethyl acetate, washed with saturated sodium bicarbonate (3×50 ml), and distilled water (3×30 ml). The aqueous solution was back extracted with ethyl acetate (2×40 ml). The combined organic layers was dried over sodium sulfate, filtered and evaporated. Flash chromatography on silica gel (1:1 ethyl acetate/hexanes) gave the 4-aminopyrimidine (320 mg, 61%). $^1$H NMR(CDCl$_3$): 5.10 (broad, 2H), 6.47 (d, 1H), 7.40 (s, 2H), 8.39 (d, 1H). Mass (ion spray): 274 (M+H).

To a solution of the 4-aminopyrimidine (184 mg, 0.67 mmol), dicyclopropyl ketone (89 mg, 0.81 mmol) and triethylamine (341 mg, 3.37 mmol) in 5 ml anhydrous dichloromethane under nitrogen was added titanium tetrachloride (167 mg, 0.88 mmol) and the resulting solution stirred for 18 hours during which time warming to room temperature was allowed. Sodium cyanoborohydride (254 mg, 4.04 mmol) in 1 ml methanol was added and the solution was stirred for 3 hours. The reaction solution was poured into water (50 ml) and extracted with dichloromethane (250 ml). The organic layer was washed with water(2×50 ml), dried over anhydrous sodium sulfate, filtered and concentrated. Flash chromatography (20% ethyl acetate/hexanes) gave secondary amine (200 mg, 81%). $^1$H NMR (CDCl$_3$): 0.2–0.7 (m, 8H), 0.9–1.1 (m, 2H), 3.2 (t, 1H), 6.31 (d, 1H), 7.38 (s, 2H), 8.25 (d, 1spray): 368 (M+H).

To a solution at the secondary amine (100 mg, 0.27 mmol) was 3 ml anhydrous dichloromethane at room temperature was added diisopropylethylamine (1.30 g, 10 mmol), propionyl chloride (76 mg, 0.82 mmol) and 4-dimethylaminopyridine (67 mg, 0.55 mmol). The reaction solution was then stirred for 36 hours. Solvent was removed under vacuum. The residue was dissolved in 250 ml ethyl acetate, washed with 1M aqueous hydrochloric acid (3×30 ml), saturated sodium bicarbonate (2×30 ml) and distilled water(2×30 ml). The aqueous solution was back extracted with ethyl acetate (2×50 ml). The combined organic layers was dried over sodium sulfate, filtered and concentrated. The product was purified by preparative TLC (20% ethyl acetate/hexanes) to give the amide (75 mg, 66%). $^1$H NMR (CDCl$_3$): 0.2–0.7 (m, 8H), 1.10 (t, 3H), 1.1–1.4 (m, 2H), 2.31 (q, 2H), 3.53 (t, 1H) 7.39 (d, 1H), 7.44(s, 2H), 8.90 (d, 1H). Mass (ion spray): 424 (M+H).

The amide (35 mg, 0.083 mmol) was dissolved in 2 ml anhydrous diethyl ether at room temperature under nitrogen. To this solution, lithium aluminum hydride (7 mg, 0.18 mmol) was added. The resulting suspension was stirred for 2 hours. The reaction solution was cooled to 0° C. 4 ml water was added slowly. The aqueous solution was extracted with diethyl ether (8 ml). The organic layer was washed with 1M aqueous hydrochloric acid (2×2 ml), saturated aqueous sodium bicarbonate (2 ml), distilled water (2×2 ml), dried over filtered and evaporated.

Preparative TLC (20% ethyl acetate/hexanes) gave 14 mg (41%) III-2.

Method E:

Some of the pyrimidine-containing compounds of the present invention are compounds in which the pyrimidine ring is fused to a cycloalkyl ring at the 4,5-positions at the pyrimidine ring. These pyrimidine compounds may be prepared by condensation of an appropriately substituted ketone (n=1,2) with a suitably substituted guanidine derivative. These pyrimidine-containing compounds may be prepared by Method E as represented schematically below.

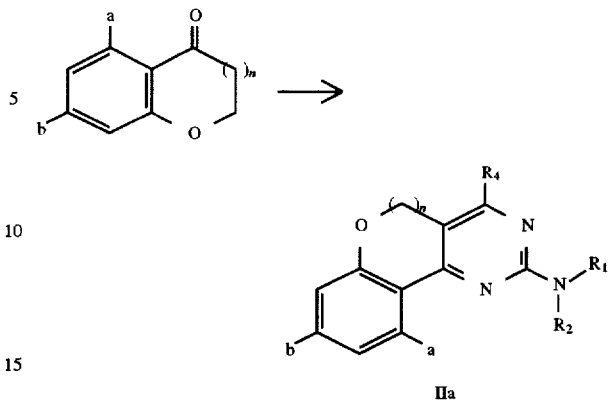

The ethyl ester of a gamma halo alkyl ester (0.051 mol), an appropriately substituted phenol (0.5 mol) and potassium carbonate (4 g) were mixed in acetonitrile (25 ml) and heated at reflux for 8 hours. The resulting mixture was cooled, filtered and evaporated to an oil. The crude oil was taken up in tetrahydrofuran (200 ml) and stirred with a solution of lithium hydroxide (4 g, 0.1 mol) in water (100 ml). After 14 hours the reaction mixture was acidified with 5M aqueous hydrochloric acid and the organic layer separated. The extract was then dried over magnesium sulfate and evaporated to dryness.

The resulting solid (4 mmol) was dissolved in polyphosphoric acid (25 g) and heated at 110° C. for 1 hour with stirring. The resulting solution was then cooled to 60° C. and poured into water (250 ml). After complete hydrolysis of the polyphosphoric acid, the aqueous solution was extracted with ethyl acetate (2×100 ml). The extracts were combined, dried over magnesium sulfate and evaporated to dryness. Flash chromatography of the residue on silica gel with 20% ethyl acetate in hexanes yields the product ketone in 20 to 40% yield.

The seven member ketone (0.1 mol) was dissolved in dimethylformamide dimethyl acetal (0.5 ml) and heated to 100° C. with stirring. After 4 hours the reaction was cooled and evaporated to a residue with a stream of dry nitrogen. The residue was taken up in ethanol (0.5 ml) and N$^1$-dicyclopropylmethyl-N$^1$-propyl guanidine hydrochloride (23 mg, 0.1 mmol) and potassium t-butoxide (12 mg, 0.1 mmol) added. The reaction was heated at 78° C. for 2 hours then cooled and evaporated to a residue. The residue was taken up in ethyl acetate (0.5 ml) and washed with water (0.5 ml). Chromatography on a 20 cm×20 cm×0.5 mm silica gel preparative plate eluting with 20% ethyl acetate in hexanes, followed by extraction gave the pyrimidine IIa.

EXAMPLE 3

Synthesis of Triazine-Containing Compounds

In this example, the preparation of triazine-containing compounds of the present invention is described. The triazine-containing compounds are prepared by Methods F and G.

Method F:

The triazine-containing compounds of the present invention (formula IV) may be prepared by sequential substitution of the chloride substituents of cyanuric chloride. Initially, chloride displacement by a suitable aryl group produces a 2,6-dichloro-4-aryl triazine. Subsequent reaction with an appropriately substituted amine provides a substituted 2-amino-4-aryl-6-chlorotriazine. Finally, substitution of the 6-chloro substituent yields the triazine compounds of the present invention. Method F is represented schematically by the following general reaction scheme.

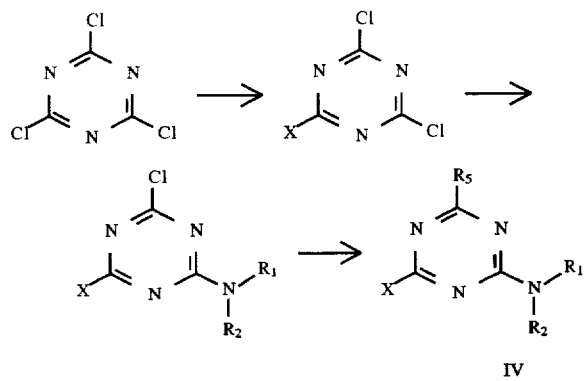

The following scheme more specifically details the preparation of triazine compounds of the present invention by Method F.

was then treated with cyanuric chloride (4.0 g, 0.027 mole) in 10 mL of tetrahydrofuran over 1 minute. This mixture was then allowed to warm to ~22° C. over 1 hour and stir for 16 hours. The dark solution was poured into water/ethyl acetate.

The organic phase was washed with 5% aqueous sodium bicarbonate and brine. The organic phase was treated with anhydrous magnesium sulfate, filtered and concentrated. The residue was then purified by flash chromatography (0 to 8% ether/hexane) to give the 2-(2',4',6'-trichlorophenyl)-4,6-dichlorotriazine (3.0 g) contaminated with some cyanuric chloride. This material was pure enough to take on to subsequent steps. $^1$H NMR (CDCl$_3$): 7.47 (s). $^{13}$C NMR (CDCl$_3$): 129.9, 135.6, 138.5, 138.6, 173.9, 175.4.

A solution of N-dicyclopropylmethyl-N-propylamine (0.6 g, 3.9 mmole) in 2 mL of tetrahydrofuran was added to a suspension of 2-(2',4', 6'-trichlorophenyl)-4,6-dichlorotriazine (0.64 g, 1.9 mmole) with stirring. A clear solution was obtained and the precipitation of the amine hydrochloride started after a few minutes. The solution was allowed to stir for 1 hour, then poured into ethyl acetate/water. The organic phase was washed with water, 0.1M

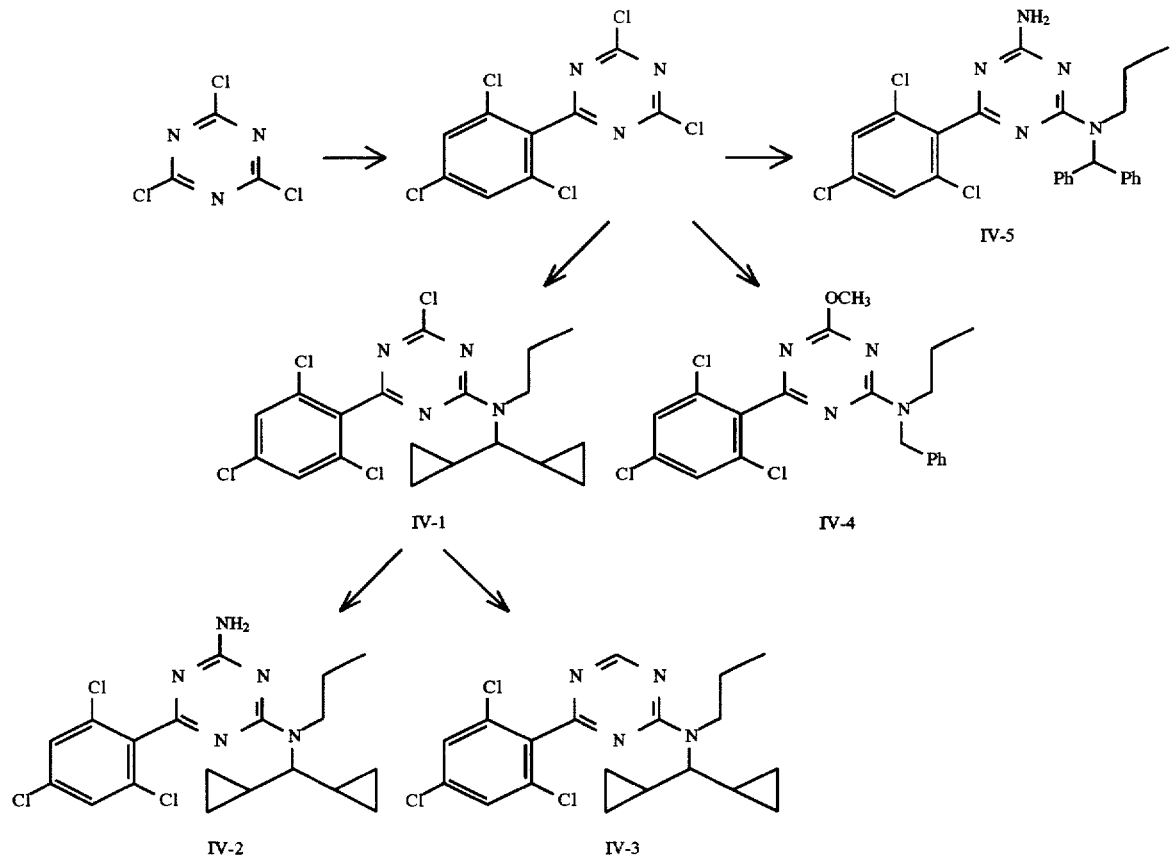

1. The Synthesis of IV-1: 2-(2',4',6'-trichlorophenyl)-4-(N-dicyclopropylmethyl-N-propylamino)-6-chlorotriazine.

A solution of 1,3,5-trichlorobenzene (3.63 g, 0.02 mole) in 40 mL of anhydrous tetrahydrofuran was stirred under nitrogen and cooled in a dry-ice bath. This solution was then treated with 12.5 mL of 1.6M solution of n-butyl lithium (0.02 mole), over 10 minutes. After stirring for 0.5 hour, the solution was treated with copper (I) iodide (1.90 g, 0.01 mole) and stirring was continued for 0.5 hour. The mixture aqueous hydrochloric acid and brine, dried over magnesium sulfate and concentrated. This gave 860 mg of IV-I as an oil (99% yield).

2. The Synthesis of IV-2: 2-(2',4',6'-trichlorophenyl)-4-(N-dicyclopropylmethyl-N-propylamino)-6-aminotriazine.

A tetrahydrofuran solution of 2-(2',4',6'-trichlorophenyl)-4-(N-dicyclopropylmethyl-N-propylamino)-6-chlorotriazine (100 mg, 0.224 mmole) in 1 mL dry tetrahydrofuran in a sealable tube was cooled to -78° C. and ~2 mL of anhydrous ammonia was added. The tube was then sealed and allow to warm to 23° C. and stir for 10 minutes. The ammonia and tetrahydrofuran were allowed to evaporate, under a stream of nitrogen, and the residue was suspended in ether. The ether suspension was filtered and the filtrate was concentrated. The residue was purified by preparative TLC (20% ethyl acetate/hexane) to give the IV-2 (60 mg, 63% yield).

3. The Synthesis of IV-3: 2-(2',4',6'-trichlorophenyl)-4-(N-dicyclopropylmethyl-N-propylamino) triazine A solution of 2-(2',4',6'-trichlorophenyl)-4-(N-dicyclopropylmethyl-N-propylamino)-6-chlorotriazine (130 mg, 0.3 mmole) in 2.5 mL of dimethylformamide was treated with sodium thiomethylate (0.04 mg, 0.57 mmole) with stirring at 23° C. for 1 hour, the mixture was then poured into ethyl acetate/water. The organic phase was washed with water, 0.1M aqueous hydrochloric acid and brine, dried over magnesium sulfate and concentrated. The residue was purified by preparative TLC (5% diethyl ether/hexane) to give 2-(2',4',6'-trichlorophenyl)-4-(N-dicyclopropylmethyl-N-propylamino)-6-methylthiotriazin (110 mg, 80% yield). $^1$H NMR (CDCl$_3$): 0.2–0.7 (bm, 8H), 0.7–1.2 (bm, 5H), 1.7–1.8 (bm, 2H), 2.3–2.6 (m, 3H), 3.2–3.5 (bm, 3H), 4.8–5.1 (bm, 2H), 7.35 (5, 1H) and 7.38 (s, 1H). Mass (ion spray): 457 (M+H).

A solution of the above compound (10 mg, 0.022 mmole) in 10 mL absolute ethanol was treated with a slurry of ~200 microliters 1:1 of Raney nickel:water. The mixture was stirred rapidly for 1 hour, then filtered and concentrated. The residue was extracted with ether, the ether suspension was filtered, concentrated and the residue purified by preparative thin-layer chromatography to provide IV-3 (1.2 mg, 13% yield).

4. The Synthesis of IV-4: 2-(2',4',6'-trichlorophenyl)-4-(N-benzyl-N-ethylamino)-6-methoxytriazine.

A solution of 2-(2',4',6'-trichlorophenyl)-4,6-dichlorotriazine (0.05 g, 0.15 mmole) in 2 mL of tetrahydrofuran was cooled in an ice-bath, and then was treated with N-benzyl-N-propylamine (0.05 mL, 0.3 mmole) in 0.5 mL of tetrahydrofuran, with stirring. The precipitation of the amine hydrochloride started immediately. The solution was allowed to stir for 30 minutes at 0° C., then allowed to warm to 23° C. and stir for an additional 30 minutes. This mixture was filtered and treated with a solution of potassium t-butoxide (100 mg, 0.89 mole) in 0.5 mL of methanol. After stirring for 16 hours, the solution was poured into ethyl acetate/water. The organic phase was washed with water, 0.1M aqueous hydrochloric acid and brine, dried over magnesium sulfate and concentrated. The residue was purified by preparative TLC (10% diethyl ether/hexane) to give the IV-4 (40 mg, 63% yield).

5. The Synthesis of IV-5: 2-(2',4',6'-trichlorophenyl)-4-(N-diphenylmethyl-N-propylamino)-6-aminotriazine.

A solution of 2-(2',4',6'-trichlorophenyl)-4,6-dichlorotriazine (0.05 g, 0.15 mmole) in 2 mL of tetrahydrofuran, was cooled in an ice-bath, and treated with N-diphenylmethyl-N-propylamine (0.05 mL, 0.3 mmole) in 0.5 mL of tetrahydrofuran, with stirring. The precipitation of the amine hydrochloride started immediately. The solution was allowed to stir for 30 minutes at 0° C., then allowed to warm to 23° C. and stir for an additional 30 minutes. The mixture was filtered and transferred to a sealable tube. This solution was cooled to −78° C. and ~5 mL of anhydrous ammonia was distilled into the tube. The tube was then sealed and allow to warm to 23° C. and stir for 16 hours. The ammonia and tetrahydrofuran were allowed to evaporate, under a stream of nitrogen, and the residue was suspended in ether. The ether suspension was filtered and the filtrate was concentrated. The residue was purified by preparative TLC (20% ethyl acetate/hexane) to give IV-5 (40 mg, 53% yield).

Method G:

Like Method F, Method G provides triazine-containing compounds from cyanuric chloride. The difference between the two methods is the sequence of chloride substitution. In Method F, the first step involves coupling an aryl group to the triazine ring while in Method G, the first step involves reaction with a suitably substituted amine. The second step in Method G couples an appropriately substituted aryl compound to the triazine ring. Accordingly, after the second steps of each method, Methods F and G both provide substituted 2-amino-4-aryl-6-chlorotriazine compounds. Method G provides 2-amino-4-aryltriazine compounds (formula IV below) and is represented schematically by the following general reaction sequence.

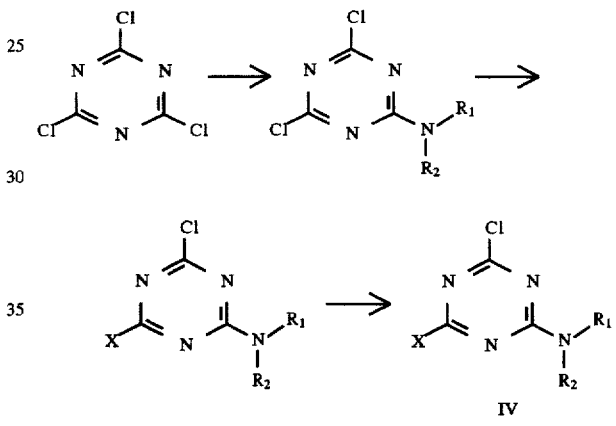

The following scheme more specifically details the preparation of a triazine-containing compound by Method G.

1. The Synthesis of IV-8: 2-(N-dicyclopropylmethyl-N-propylamino)-4-(2',4'-dichlorophenyl)triazine.

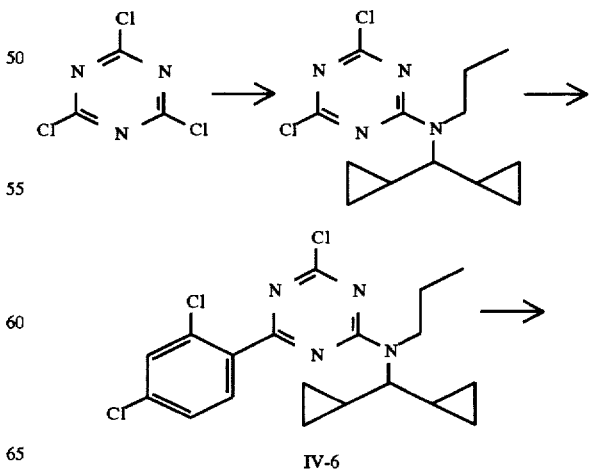

IV-6

-continued

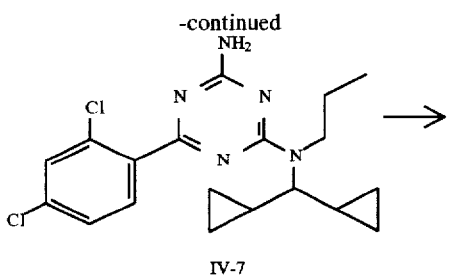

IV-7

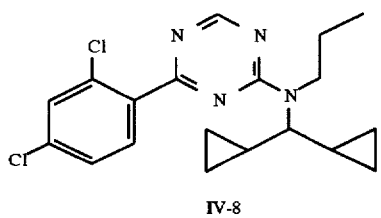

IV-8

To a solution of cyanuric chloride (0.737 g, 4.4 mmol) in 5 ml dry tetrahydrofuran was added (0.35 ml, 2 mmol) N,N-diisopropylethylamine and (0.75 g, 4.9 mmol) of N-propyl-N-dicyclopropylmethylamine at room temperature with stirring under nitrogen. After 1 hour the resulting suspension was partitioned between 0.5M aqueous hydrochloric acid and ethyl ether and the organics washed with brine and dried over magnesium sulfate. The crude product was chromatographed on silica gel using 10% diethyl ether/hexanes to give the substituted 2-aminotriazine as a white solid (0.6 g, 50%). $^1$H NMR (CDCl$_3$): 3.52–3.62 (q, 2H), 1.75–1.85 (m, 2H), 1.05–1.2 (m, 2H), 0.95–1.05 (t, 3H), 0.65–0.8 (m, 2H), 0.4–0.6 (m, 4H), 0.25–0.35 (m, 2H)

A solution of the substituted 2-aminotriazine (1.94 g, 6.44 mmol), 2,4-dichlorobenzene boronic acid (1.35 g, 7.08 mmol), tetrakis(triphenyl phosphine)palladium (1.49 g, 1.29 mmol), sodium carbonate (2.05 g, 19.3 mmol) in 30 ml of benzene/water/ethanol (10:4:1) was refluxed under nitrogen with stirring for 12 hours. The solvent was removed and the residue was partitioned between diethyl ether and water. The ether solution was dried over magnesium sulfate. The crude product was chromatographed on silica using 1:1 toluene/hexanes to give the substituted 2-amino-4-aryltriazine IV-6 as an oil (1.4g, 53%). $^1$H NMR (CDCl$_3$): 7.85–7.95 (d, 1H) 7.4–7.5 (t, 1H), 7.25–7.35 (t, 1H), 3.4–3.6 (t, 2H), 1.7–1.9 (m, 2H), 1.0–1.2 (m 2H), 1.2–1.2 (m,2H), 0.9–1.05 (t; 3H), 0.55–0.75 (m, 2H), 0.2–0.55 (m, 6H).

A solution of the substituted 2-amino-4-aryltriazine IV-6 (0.1 g, 0.24 mmol) in 2 ml dry tetrahydrofuran was cooled to –60° C. in a sealable tube followed by the addition of 2 ml of ammonia. The tube was sealed and allowed to stir while warming to room temperature for a total of 3 hours. The resulting solution was concentrated in vacuo and purified column chromatography with silica gel using diethyl ether and hexanes to give the substituted 2-amino-4-aryl-6-aminotriazine IV-7 (60 mg, 64%). $^1$H NMR (CDCl$_3$): 7.6–7.75 (d, 1H), 7.4–7.5 (2s, 1H), 7.2–7.35 (2d, 1H), 4.9–5.1 (2s, 2H), 3.4–3.6 (t, 2H), 1.7–1.9 (m, 2H), 1.0–1.2 (m, 2H), 0.85–1.05 (2t, 3H), 0.55–0.7 (m, 2H), 0.2–0.5 (m, 6H).

To a solution of butyl nitrite (11 mg, 0.10 mmol) in 1.0 ml dry N,N-dimethylformamide was added the substituted 2-amino-4-aryl-6-aminotriazine IV-7 (27 mg, 0.07 mmol) under nitrogen with stirring. The colorless reaction mix was heated at 40° C. for 2 hours. The resulting yellow solution was partitioned between diethyl ether/water and the ether solution was dried over magnesium sulfate. The crude reaction was purified on silica gel using 10% ethyl ether/hexanes to give IV-8 as an oil.

EXAMPLE 4

Synthesis of Triazole-Containing Compounds

In this example, the preparation of triazole-containing compounds of the resent invention is described. The triazole-containing compounds are prepared by method H as represented below.

Method H:

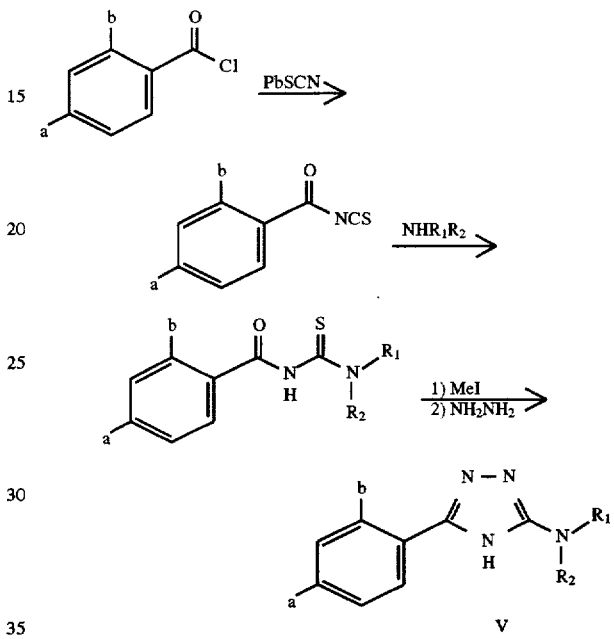

Method H provides the triazole-containing compounds of the present invention in three steps. In the first step, benzoyl chloride is converted to the corresponding isothiocyanate by reaction with lead thiocyanate. The isothiocyanate is then reacted with an appropriately substituted amine in the second step to yield the corresponding thiourea which, in the third step, is then treated with methyl iodide and then hydrazine to produce the 2-amino-5-aryltriazole compound of structure V.

In a related method, triazole-containing compounds of structure VI may be prepared by modifying the reaction scheme of Method H. Specifically, compounds of structure VI may be synthesized by modifying Method H to methylhydrazine (i.e., NH(R$_6$)NH$_2$, where R$_6$=methyl) in place of hydrazine.

The following reactions exemplify the synthesis of a triazole-containing compound of V-1 by Method H.

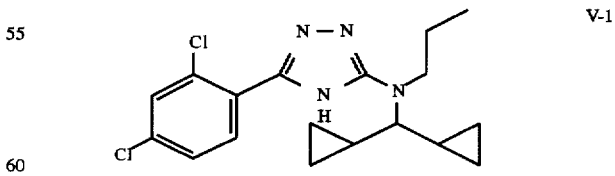

1. The Synthesis of N-(2,4-Dichlorobenzoyl)-N'-(propyl)-N'-(dicyclopropylmethyl) thiourea.

2,4-Dichlorobenzoyl chloride (2.1 g, 10 mmol) and lead thiocyanate (1.62 g, 5 mmol) were added to toluene (10 ml) and the mixture was heated at reflux for 16 hours. The reaction mixture turned yellow and the insoluble lead salt was removed by filtration. The solid was washed with toluene (5 ml) and the yellow filtrate containing the isothiocyanate was treated with N-dicyclopropymethyl-N-propylamine (2.3 g., 15 mmol). An exothermic reaction ensued and TLC (ethyl acetate: hexane 1:10) of the reaction mixture showed disappearance of starting material and the formation of a single new slower moving spot. Flash silica gel (10 ml) was added to the reaction and the mixture was evaporated to a powder. The powder was added to the top of a flash silica gel column (150 ml) packed with ethyl acetate: hexane (1:10) and the column was eluted with the same solvent pair. The fractions containing product were combined and evaporated to a white foam (1.9 g, 49%) that was used directly in the next step.

2. The Synthesis of 3-(N-Propyl-N-dicyclopropmethyl) amino-5-(2,4-dichlorophenyl)-1,2,4-triazole (V-1).

The above thiourea (1.75 g, 4.54 mmol) was dissolved in methylene chloride (20 ml) and treated with methyl iodide (1 ml) at room temperature for 16 hours. The resulting oil that separated from the reaction was diluted with hexane (20 ml) and the solution was decanted from the oil. The oil was dissolved in methanolic (10 ml) sodium methoxide (125 mg, 5.45 mmol). Hydrazine (320 mg, 10 mmol) was added and the light yellow solution was heated at a reflux for 24 hours, poured into water (50 ml) and stirred at room temperature. The resulting white crystalline solid (1.5 g, 90%) was collected by filtration and washed with water and dried in vacuo to give V-1, mp 148° C.–149° C.

EXAMPLE 5
Representative Compounds

Representative thiadiazole-, pyrimidine-, triazine-, and triazole-containing compounds of this invention are set forth in Tables 1 through 5 below.

TABLE 1

Representative Thiadiazole-Containing Compounds

| Compound | $R_1$ | $R_2$ | X |
|---|---|---|---|
| I-1 | $nC_3H_7$ | dicyclopropylmethyl | 2,4-dichlorophenyl |
| I-2 | $nC_3H_7$ | dicyclopropylmethyl | 2,4,6-trichlorophenyl |

TABLE 2

Representative Pyrimidine-Containing Compounds

| Compound | $R_1$ | $R_2$ | $R_3$ | $R_4$ | X |
|---|---|---|---|---|---|
| II-1 | $nC_3H_7$ | dicyclopropylmethyl | H | H | 2,4-dichlorophenyl |
| II-2 | $nC_3H_7$ | dicyclopropylmethyl | $CH_3$ | H | 2,4-dichlorophenyl |
| II-3 | $nC_3H_7$ | dicyclopropylmethyl | H | $CH_3$ | 2,4-dichlorophenyl |
| II-4 | $nC_3H_7$ | dicyclopropylmethyl | F | H | 2,4-dichlorophenyl |

TABLE 2-continued

Representative Pyrimidine-Containing Compounds

| Compound | $R_1$ | $R_2$ | $R_3$ | $R_4$ | X |
|---|---|---|---|---|---|
| II-5 | $nC_3H_7$ | dicyclopropylmethyl | Cl | H | 2,4-dichlorophenyl |
| II-6 | $nC_3H_7$ | dicyclopropylmethyl | H | Cl | 2,4-dichlorophenyl |
| II-7 | $nC_3H_7$ | dicyclopropylmethyl | $CH_3$ | H | 4-chlorophenyl |
| II-8 | $nC_3H_7$ | dicyclopropylmethyl | Br | H | 4-chlorophenyl |
| II-9 | $nC_3H_7$ | dicyclopropylmethyl | H | H | 4-chlorophenyl |
| II-10 | $nC_3H_7$ | dicyclopropylmethyl | $-C(=O)N(CH_3)_2$ | H | 2,4-dichlorophenyl |
| II-11 | $nC_3H_7$ | dicyclopropylmethyl | H | H | 2,4,6-trichlorophenyl |
| II-12 | $nC_3H_7$ | dicyclopropylmethyl | $-C(=O)N(CH_3)_2$ | H | 2,4-dichlorophenyl |
| II-13 | $nC_3H_7$ | dicyclopropylmethyl | $-SO_2CH_3$ | H | 2,4-dichlorophenyl |
| II-14 | $nC_3H_7$ | dicyclopropylmethyl | $-SOCH_3$ | H | 2,4-dichlorophenyl |

TABLE 2-continued

Representative Pyrimidine-Containing Compounds

II

| Compound | R₁ | R₂ | R₃ | R₄ | X |
|---|---|---|---|---|---|
| II-15 | nC₃H₇ | dicyclopropylmethyl | CH₂CH₃ | H | 2,4-dichlorophenyl |
| II-16 | nC₃H₇ | dicyclopropylmethyl | CH₃ | H | 4-bromophenyl |
| II-17 | nC₃H₇ | dicyclopropylmethyl | CH₃ | H | 4-methoxyphenyl |
| II-18 | nC₃H₇ | dicyclopropylmethyl | H | H | 4-iodophenyl |
| II-19 | nC₃H₇ | dicyclopropylmethyl | CH₃ | H | 3,4-dichlorophenyl |
| II-20 | nC₃H₇ | dicyclopropylmethyl | H | H | 2,4-dimethoxyphenyl |
| II-21 | nC₃H₇ | dicyclopropylmethyl | H | H | 2,3-dichlorophenyl |
| II-22 | nC₃H₇ | dicyclopropylmethyl | H | H | 2,4,6-trimethoxyphenyl |
| II-23 | nC₃H₇ | dicyclopropylmethyl | H | H | 2,3-dimethoxyphenyl |
| II-24 | nC₃H₇ | dicyclopropylmethyl | H | H | 2,4,6-trimethylphenyl |

TABLE 2-continued

Representative Pyrimidine-Containing Compounds

II

| Compound | R₁ | R₂ | R₃ | R₄ | X |
|---|---|---|---|---|---|
| II-25 | nC₃H₇ | dicyclopropylmethyl | CH₃ | H | 2,4,6-trimethoxyphenyl (2,4,6-tri-OCH₃-C₆H₂) |
| II-26 | nC₃H₇ | dicyclopropylmethyl | H | H | 2,5-dimethylphenyl |
| II-27 | nC₃H₇ | dicyclopropylmethyl | H | H | 4-chloro-2-methoxyphenyl |
| II-28 | nC₃H₇ | dicyclopropylmethyl | H | H | 4-bromophenyl |
| II-29 | nC₃H₇ | dicyclopropylmethyl | CH₃ | H | 2-fluorophenyl |
| II-30 | nC₃H₇ | dicyclopropylmethyl | CH₃ | H | phenyl |
| II-31 | nC₃H₇ | cyclopropylmethyl | H | H | 2,4-dichlorophenyl |
| II-32 | nC₃H₇ | dicyclopropylmethyl | CH₃ | H | 4-chloro-2-methoxyphenyl |
| II-33 | nC₃H₇ | dicyclopropylmethyl | (see X) | H | 2,4-dichloro-6-propoxyphenyl |

TABLE 2-continued

Representative Pyrimidine-Containing Compounds

II (Structure: pyrimidine with R3, R4 on positions, X at 4-position, and C(=N)-N(R1)(R2) at 2-position)

| Compound | R₁ | R₂ | R₃ | R₄ | X |
|----------|-----|-----|-----|-----|---|
| II-34 | nC₃H₇ | dicyclopropylmethyl | (see X) | H | 2-(n-propoxy)-3,5-dimethoxyphenyl (with CH₃O groups) |
| II-35 | nC₃H₇ | dicyclopropylmethyl | H | H | 4-chloro-2,6-dimethoxyphenyl |
| II-36 | nC₃H₇ | dicyclopropylmethyl | H | H | 3-chloro-2,5-dimethoxyphenyl |
| II-37 | nC₃H₇ | dicyclopropylmethyl | CH₃ | H | 4-fluorophenyl |
| II-38 | nC₃H₇ | cyclopropylethyl | CH₃ | H | 4-bromophenyl |
| II-39 | nC₃H₇ | dicyclopropylmethyl | CH₃ | H | 2,4-dimethoxyphenyl |
| II-40 | nC₃H₇ | dicyclopropylmethyl | CH₃ | H | 2-phenylphenyl (biphenyl) |
| II-41 | nC₃H₇ | dicyclopropylmethyl | —CO₂CH₃ | H | 2,6-dimethoxyphenyl |

TABLE 2-continued
Representative Pyrimidine-Containing Compounds
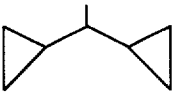
| Compound | R₁ | R₂ | R₃ | R₄ | X |
|---|---|---|---|---|---|
| II-42 | nC₃H₇ | 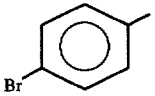 | CH₃ | CH₃ | 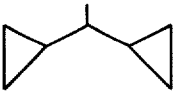 |
| II-43 | nC₃H₇ | 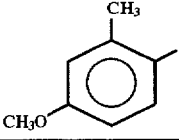 | H | H | 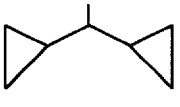 |
TABLE 3
Representative Pyrimidine-Containing Compounds
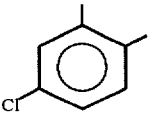
| Compound | R₁ | R₂ | R₃ | R₄ | X |
|---|---|---|---|---|---|
| III-1 | nC₃H₇ | 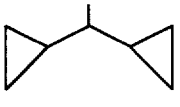 | H | H | 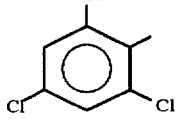 |
| III-2 | nC₃H₇ | 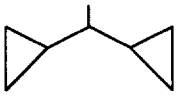 | H | H | 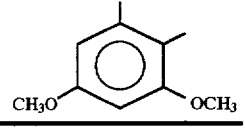 |
| III-3 | nC₃H₇ | | H | H | |

TABLE 4

Representative Triazine-Containing Compounds

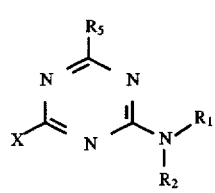

IV

| Compound | $R_1$ | $R_2$ | $R_5$ | X |
|---|---|---|---|---|
| IV-1 | $nC_3H_7$ | dicyclopropylmethyl | Cl | 2,4,6-trichlorophenyl |
| IV-2 | $nC_3H_7$ | dicyclopropylmethyl | $NH_2$ | 2,4,6-trichlorophenyl |
| IV-3 | $nC_3H_7$ | dicyclopropylmethyl | H | 2,4,6-trichlorophenyl |
| IV-4 | $nC_2H_5$ | CH(CH3)Ph | $OCH_3$ | 2,4,6-trichlorophenyl |
| IV-5 | $nC_3H_7$ | CH(Ph)(Ph) | $NH_2$ | 2,4,6-trichlorophenyl |
| IV-6 | $nC_3H_7$ | dicyclopropylmethyl | Cl | 2,4-dichlorophenyl |
| IV-7 | $nC_3H_7$ | dicyclopropylmethyl | $NH_2$ | 2,4-dichlorophenyl |
| IV-8 | $nC_3H_7$ | dicyclopropylmethyl | H | 2,4-dichlorophenyl |

TABLE 5

Representative Triazole-Containing Compounds

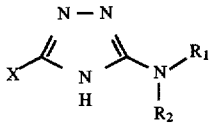

| Compound | R₁ | R₂ | R₆ | X |
|---|---|---|---|---|
| V-1 | nC₃H₇ | (dicyclopropylmethyl) | — | 2,4-diClC₆H₃ |
| VI-1 | nC₃H₇ | (dicyclopropylmethyl) | CH₃ | 2,4-diClC₆H₃ |

EXAMPLE 6

Analytical Data of Representative Compounds

This example presents (in Table 6) $^1$H NMR and mass spectral (MS) data for representative thiadiazole-, pyrimidine-, triazine-, and triazole-containing compounds listed in Tables 1 through 5 of Example 5. The $^1$H NMR spectra were recorded as CDCl₃ solutions and chemical shifts are reported in ppm downfield from tetramethylsilane. The mass spectra (MS) were obtained by ion spray mass spectrometry unless otherwise indicated. EI-MS refers to mass spectra obtained by electron impact mass spectrometry. The mass spectra reported refer to molecular ions (M) unless otherwise indicated.

TABLE 6

Analytical Data of Representative Compounds

| Compound | $^1$H NMR | MS |
|---|---|---|
| I-1 | 0.45(m, 7H), 0.69(m, 2H), 1.05(t, 3H), 1.15(m, 2H), 1.87(m, 2H), 3.45(t, 2H), 7.28(d, 1H), 7.42(s, 1H), 7.78(d, 1H) | 383 |
| I-2 | 0.45(m, 7H), 0.69(M, 2H), 1.05(t, 3H), 1.19(m, 2H), 1.88(m, 2H), 3.49(t, 2H), 7.39(s, 2H) | 417 |
| II-1 | 0.35(m, 4H), 0.43(m, 2H), 0.62(m, 2H), 0.95(t, 3H), 0.91–1.21(br, 2H), 1.80(m, 2H), 3.55(t, 2H), 3.55–3.75(br, 1H), 6.68–6.80(br, 1H), 7.34(d, 1H), 7.46(s, 1H), 7.60(m, 1H), 8.20–8.38(br, 1H) | EI-MS: 375, 377 |
| II-2 | 0.31(m, 4H), 0.38(m, 2H), 0.58(m, 2H), 0.93(t, 3H), 1.10(m, 2H), 1.77(m, 2H), 1.94 t(s, 3H), 3.51(t, 2H), 3.50–3.70(br, 1H), 7.18(d, 1H), 7.32(d, d, 1H), 7.47(d, 1H), 8.14(s, 1H) | 390 |

TABLE 6-continued

Analytical Data of Representative Compounds

| Compound | $^1$H NMR | MS |
|---|---|---|
| II-3 | 0.35(m, 4H), 0.43(m, 2H), 0.62(m, 2H), 0.96(t, 3H), 1.06–1.22(br, 2H), 1.82(m, 2H), 2.34(s, 3H), 3.57(t, 2H), 3.70–3.85(br, 1H), 6.61(s, 1H), 7.32(d, 1H), 7.46(d, 1H), 7.40–7.60(br, 1H) | 390 |
| II-4 | 0.29(m, 2H), 0.38(m, 4H), 0.61(m, 2H), 0.93(t, 3H), 1.09(m, 2H), 1.77(m, 2H), 3.50(t, 2H), 3.40–3.60(br, 1H) 7.36(m, 2H), 7.50(s, 1H), 8.17(s, 1H) | 394 |
| II-5 | 0.26(m, 2H), 0.35(m, 4H), 0.61(m, 2H), 0.92(t, 3H), 1.08(m, 2H), 1.76(m, 2H), 3.49(t, 2H), 3.40–3.60(br, 1H) 2.25(br, 1H), 7.43(d, 1H), 7.48(s, 1H), 8.10–8.55(br, 1H) | 410 |
| II-6 | 0.36(m, 6H), 0.63(m, 2H), 0.95(t, 3H), 1.00–1.20(br, 2H) 1.79(m, 2H), 3.54(t, 2H), 3.40–3.60(br, 1H), 6.65–6.80(br, 1H), 7.28–7.40(br, 2H), 7.47(s, 1H) | 410 |
| II-7 | 0.30(m, 4H), 0.42(m, 2H), 0.60(m, 2H), 0.95(t, 3H), 1.03–1.18(br, 2H), 1.79(m, 2H), 2.16(s, 3H), 3.54(t, 2H), 3.60–3.75(br, 1H), 7.41(d, 2H), 7.55(d, 2H) 8.11(s, 1H) | 356 |
| II-8 | 0.29(m, 2H), 0.37(m, 4H), 0.63(m, 2H), 0.96(t, 3H), 1.00–1.21(br, 2H), 1.79(m, 2H), 3.54(t, 2H), 350–3.70(br, 1H), 7.43(d, 2H), 7.60–7.90(br, 2H), 8.20–8.45(br, 1H) | EI-MS: 419, 421 |
| II-9 | 0.35(m, 4H), 0.48(m, 2H), 0.64(m, 2H), 1.00(t, 3H), 1.00–1.25(br, 2H), 1.83(m, 2H), 3.61(t, 2H), 3.50–3.90(br, 1H), 6.78(d, 1H), 7.41(d, 2H), 7.80–8.05(br, 2H), 8.20–8.35(br, 1H) | EI-MS: 410 |
| II-10 | 0.3(bm, 6H), 0.6(bm, 2H), 0.9(bm, 3H), 1.1(bm, 2H), 1.8(bm, 2H), 1.95(s, 3H), 3.28(bm, 1H), 3.5(t, 2H), 6.61(bs, 1H), 7.32(bs, 1H), 7.5(s, 1H), 8.4(bs, 1H) | EI-MS: 432 |
| II-11 | 0.2–0.5(m, 6H), 0.59(m, 2H), 0.93(m, 3H), 1.08(m, 2H), 1.78(m, 2H), 3.51(t, 2H), 6.33(d, 2H), 7.26(s, 1H), 7.38(s, 1H), 8.35(m, 1H) | 401 |
| II-12 | 0.2–0.55(m, 6H), 0.63(m, 2H), 0.86(t, 2H), 0.96(t, 2H), 1.08(m, 2H), 1.77(m, 2H), 3.60(m, 2H) 5.30(s, 3H), 7.08(d, 1H) 7.26(m, 1H), 7.38(d, 1H), 8.80(d, 1H) | 447 |
| II-13 | 0.2–0.5(m, 7H), 0.65(m, 2H), 0.85(t, 1H), 1.0(t, 1H), 1.1(m, 2H), 1.80(m, 3H), 2.80(s, 3H), 3.60(m, 2H), 7.25(s, 1H), 7.30(d, 1H), 7.45(d, 1H), 8.75 (s, ½H), 8.90(s, ½H) | M + H: 454, 456<br>M + NA: 476, 478 |
| II-14 | 0.2–0.5(m, 7H), 0.75(m, 2H), 0.90(t, 1H), 1.0(t, 1H), 1.12(m, 2H), 1.78(m, 3H), 2.66(s, 3H), 3.60(m, 2H), 7.27(d, 1H), 7.36(d, 1H), 7.49(d, 1H), 8.75(s, ½H), 8.90(s, ½H) | M + Na: 460, 462 |
| II-15 | 0.25–1.85(m, 21H), 2.25 (q, 2H), 3.50 (m, 2H), 3.61(brs, 1H), 7.18(d, 1H), 7.31(dd, 1H), 7.46(d, 1H), 8.20(brs, 1H) | 404 |
| II-16 | 0.28(m, 2H), 0.50(m, 2H), 0.92(t, 3H), 1.15(m, 1H), 1.65(m, 2H), 3.50(d, 2H), 3.62(m, 2H), 3.50(d, 2H), 3.62(m, 2H), 7.51(d, 2H), 7.86(d, 2H), 8.15(s, 1H), | 360 |
| II-17 | 0.25–1.85(m, 18H), 2.20(s, 3H), 3.54(m, 2H), 3.70(m, 1H), 3.97(s, 3H), 6.97(d, 2H), 7.62(d, 2H), 8.08(s, 1H) | 352 |
| II-18 | 0.25–1.85(m, 18H), 3.60(m, 2H), 3.70(m, 1H), 6.82(d, 1H), 7.80(m, 4H), 8.30(brs, 1H) | 434 |
| II-19 | 0.25–1.82(m, 18H), 2.16(s, 3H), 3.52(m, 2H), 3.62 (m, 1H), 7.45(brs, 1H), 7.51(d, 1H), 7.70(brs, 1H), 8.12(brs, 1H) | 390 |
| II-20 | 0.30–1.90(m, 18H), 3.60(m, 2H), 3.75(m, 1H), 3.88 (s, 6H), 6.54(s, 1H), 6.62(d, 1H), 7.08(d, 1H), 8.00 (brs, 1H), 8.20(brs, 1H) | 369 |
| II-21 | 0.25–1.85(m, 18H), 3.54(m, 2H), 3.70(m, 1H), 6.64 (brs, 1H), 7.44(d, 1H), 7.46(d, 1H), 8.30(brs, 1H) | 410 |
| II-22 | 0.2–0.7(m, 8H), 0.94(t, 3H), 1.0–1.2(m, 2H), 1.7–1.9(m, 2H), 3.40–3.60(m, 3H), 3.74(s, 6H), 3.86(s, 3H), 6.20(s, 2H), 6.42(d, 1H), 8.24(d, 1H) | 398 |
| II-23 | 0.20–0.65(m, 8H), 0.93(t, 3H), 1.0–1.2(m, 2H), | M + H: |

TABLE 6-continued

Analytical Data of Representative Compounds

| Compound | $^1$H NMR | MS |
|---|---|---|
|  | 1.6–1.9(m, 2H), 3.4–3.6(m, 3H), 3.74(s, 6H), 6.41(d, 1H), 6.63(d, 2H), 7.30(t, 1H), 8.26(d, 1H) | 368; M + Na: 390 |
| II-24 | 0.2–0.7(m, 8H), 0.8–1.2(m, 5H), 1.5–1.9(m, 2H) 2.1(s, 6H), 2.32(s, 3H), 3.4–3.8(m, 3H), 6.28(d, 1H), 6.91(s, 2H), 8.26(broad, 1H) | M + H: 350; M + Na: 372 |
| II-25 | 0.2–0.6(m, 8H), 0.91(t, 3H), 1.0–1.1(m, 2H), 1.5–1.9(m, 2H), 1.84(s, 3H), 3.4–3.6(m, 3H), 3.71(s, 6H), 3.85(s, 3H), 6.18(s, 2H), 8.08(s, 1H) | M + H: 412; M + Na: 434 |
| II-26 | — | M + H: 336; M + Na: 358 |
| II-27 | 0.35(bm, 4H), 0.45(bm, 2H), 0.6(bm, 2H), 0.85(bm, 2H), 0.95(t, 3H), 1.8(bm, 2H), 2.05(bm, 1H), 3.55(t, 2H), 3.85(s, 3H), 5.35(s, 1H), 6.95(s, 1H), 7.05(m, 2H), 8.23(bm, 1H) | M + Na: 394 |
| II-28 | 0.3–0.45(m, 4H), 0.4–0.55(m, 4H), 0.6–0.75(m, 2H), 0.95–1.1(t, 3H), 1.05–1.25(m, 1H), 1.75–1.95(m, 2H), 3.6–3.7(t, 2H), 6.8–6.9(d, 2H), 7.65–7.75(d, 2H),7.8–8.0(d, 1H), 8.2–8.4(d, 1H) | 387 |
| II-29 | 0.25–0.45(m, 6H), 0.55–0.65(m, 3H), 0.85–1.0(t, 3H), 1.05–1.15(m, 4H), 1.25(s, 3H), 3.45–3.55(t, 2H), 7.1–7.2(t, 1H), 7.2–7.3(t, 1H), 7.35–7.5(m, 2H), 8.1(s, 1H) | 340 |
| II-30 | 0.2–0.5(m, 6H), 0.55–0.7(m, 3H), 0.85–1.05(t, 3H), 1.0–1.2(m, 2H), 1.7–1.9(m, 2H), 2.45(s, 3H), 3.55(t, 2H), 7.2–7.4(m, 5H), 8.25(s, 1H) | 322 |
| II-31 | 0.29(d, 2H), 0.50(d, 2H), 0.94(t, 3H), 1.15(m, 1H), 1.69(m, 2H), 3.53(d, 2H), 3.63(t, 2H), 6.78(d, 1H), 7.33(d, 1H), 7.47(s, 1H), 7.58(d, 1H), 8.35(d, 1H) | EI-MS: 335, 337 |
| II-32 | 0.4(m, 4H), 0.42(m, 2H), 0.59(m, 2H), 0.95(t, 3H), 1.1(bm, 2H), 1.75(m, 2H), 1.9(s, 3H), 3.5(t, 2H), 3.65(bm, 1H), 3.8(3H, s), 6.95(s, 1H), 7.1(m, 2H), 8.05(s, 1H) | EI-MS: 385 |
| II-33 | 0.35(bm, 4H), 0.45(bm, 2H), 0.65(bm, 2H), 1.05(t, 3H), 1.15(bm, 2H), 1.85(m, 2H), 2.6(t, 2H), 3.55(m, 2H), 3.8(bm, 1H), 4.4(t, 2H), 7.1(m, 1H), 7.35(m, 1H), 8.2(bs, 1H) | EI-MS: 417 |
| II-34 | 0.4(bm, 6H), 0.65(bm, 2H), 1.9(bm, 2H), 2.67(t, 2H), 3.55(m, 2H), 3.8(bm, 1H), 3.82(s, 3H), 3.88(s, 3H), 4.42(t, 2H), 6.35(m, 1H), 6.45(m, 1H), 8.15(bs, 1H) | EI-MS: 409 |
| II-35 | 0.3(6H), 0.65(m, 2H), 0.92(t, 3H), 1.05(bm, 2H), 1.8(m, 2H), 3.55(t, 2H), 3.7(bs, 1H), 3.75(s, 6H), 6.39(d, 1H) 6.65(s, 2H), 8.25(bs, 1H) | EI-MS: 401 |
| II-36 | 0.3(bm, 6H), 0.65(bm, 2H), 0.92(m, 3H), 1.05(bm, 2H) 1.8(bm, 2H), 3.55(t, 2H), 3.7(bs, 1H), 3.75(s, 3H), 3.85, (s, 3H), 6.39(d, 1H), 6.42(m, 1H), 6.52(m, 1H), 8.3(bs, 1H) | EI-MS: 411 |
| II-37 | 0.25–1.85(m, 1H), 2.20(s, 3H), 3.57(m, 2H), 3.70(brs, 1H), 7.16(m, 2H), 7.62(brs, 2H), 8.12(brs, 1H) | — |
| II-38 | 0.25–1.85(m, 18H), 2.16(s, 3H), 3.51(m, 2H), 3.68(m, 1H), 7.50(brs, 2H), 7.57(d, 2H), 8.10(brs, 1H) | 400 |
| II-39 | 0.25–1.85(brs., 18H), 1.93(s, 3H), 3.53(m, 2H), 3.70(brs, 1H), 3.79(s, 3H), 3.86(s, 3H), 6.52(d, 1H), 6.58(dd, 1H), 7.20(d, 1H), 8.08(brs, 1H) | 382 |
| II-40 | 0.25–1.85(m, 18H), 1.61(s, 3H), 3.4–3.65(m, 3H), 7.15–7.50(m, 9H), 7.9(brs, 1H) | 398 (M + 1) |
| II-42 | 0.25–1.85(m, 18H), 2.08(s, 3H), 2.33(s, 3H), 3.52(m, 2H), 3.65(m, 1H), 7.40(d, 2H), 7.56(d, 2H) | 413, 415 (M + 1) |
| III-1 | 0.2–0.8(m, 8H), 0.95(t, 3H), 0.90–1.10(m, 2H), 1.60–1.80(m, 2H), 3.2–3.6(m, 3H), 6.26(d, 1H), 7.30(d, 1H), 7.45 (s, 1H), 7.68(d, 1H), 8.22(d, 1H) | 376 |
| III-3 | 0.2–0.7(m, H), 0.90(t, 3H), 0.95–1.20(m, 2H), 1.7–1.9(m, 2H), 3.3–3.5(m, 3H), 6.28(d, 1H), 7.35(s, 2H), 8.22(d, 1H) | M + H: 440; M + Na: 432 |
| IV-1 | 0.2–0.8(bm, 8H), 0.8–1.2(bm, 5H), 1.2–2.8(bm, 2H), 3.3–3.7(bm, 3H), 4.8–5.1(bm, 2H), 7.38, 7.43 and 7.52(3s, 2H) | 445 |
| IV-2 | 0.2–0.7(bm, 8H), 0.7–1.2(bm, 5H), 1.2–2.8(bm, 2H), 3.2–3.5(bm, 3H), 4.8–5.1(bm, 2H), 7.35 and 7.38 (2s, 2H) | 426 |
| IV-3 | — | EI-MS: 411, 412 |
| IV-4 | 1.2(m, 3H), 0.7–1.2(bm, 5H), 3.62(m, 2H), 3.95 and 4.06(2s, 3H),4.87 and 4.93(2s, 2H), 7.2–7.5 (m, 7H) | M + H: 423; M + Na: 445 |
| IV-5 | 0.4–1.1(bm, 2H), 1.23(t, 3H), 3.3–3.6(m,2H), 5.2 (bs, 1H), 7.2–7.5(m, 12H). |  |
| IV-6 | 0.2–0.55(m, 6H), 0.55–0.75(m, 2H), 0.9–1.05(t, 3H),1.0–1.2(m, 2H), 1.7–1.9(m, 2H), 3.4–3.6(t, 2H),7.25–7.35(t, 1H), 7.4–7.5(t, 1H), 7.85–7.95(2d, 1H) | 412 |
| IV-7 | 0.2–0.5(m, 6H), 0.55–0.7(m, 2H), 0.85–1.05(t, 3H), 1.0–1.2(m, 2H), 1.7–1.9(m, 2H), 3.4–3.6(t, 2H), 4.9–5.1(2s, 2H), 7.2–7.35(2d, 1H), 7.4–7.5(2s, 1H), 7.6–7.75(2d, 1H) | 392, 393 |
| IV-8 | 0.2–0.6(m, 6H), 0.6–0.8(m, 2H), 0.8–1.44(m, 6H), 1.75–1.9(m, 2H), 3.55–3.65(t, 2H), 7.3–7.4(d, 1H), 8.45–8.55(s, 1H), 8.6–8.8(d, 1H), 8.55–8.7(s, 1H) | 378 |
| V-1 | 0.25–0.5(m, 7H), 0.65(m, 2H), 0.95(t, 3H), 1.1(m, 2H), 1.8(m, 2H), 3.03(t, 1H), 3.4(t, 2H), 7.30(d, 1H), 7.35(d, 1H), 7.47(d, 1H), 7.93(bs, 1H) | 365 |

EXAMPLE 7

Representative Compounds Having CRF Receptor Binding Activity

This example identifies representative compounds of this invention having CRF receptor binding activity ($K_i$) of equal to or less than 250 nM. Compounds were evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay was performed in 1.5 ml Eppendorf tubes using approximately $1 \times 10^6$ cells per tube stably transfected with human CRF receptors. Each tube received about 0.1 ml of assay buffer (e.g., Dulbecco's phosphate buffered saline, 10 mM magnesium chloride, 20 μM bacitracin) with or without unlabeled sauvagine, urotensin I or CRF (final concentration, 1 μM) to determine nonspecific binding. 0.1 ml of [$^{125}$I] tyrosine—ovine CRF (final concentration ~200 pM or approximately the $K_D$ as determined by Scatchard analysis) and 0.1 ml of a membrane suspension of cells containing the CRF receptor. The mixture was incubated for 2 hours at 22° C. followed by the separation of the bound and free radioligand by centrifugation. Following two washes of the pellets, the tubes were cut just above the pellet and monitored in a gamma counter for radioactivity at approximately 80% efficiency. All radioligand binding data was analyzed using the non-linear least-square curve-fitting program LIGAND of Munson and Rodbard (*Anal. Biochem.* 107:220, 1990).

Representative compounds of the present invention having a $K_i \leq 250$ nM are listed in Table 7 below. Binding activity corresponds to the concentration (nM) of the compound necessary to displace 50% of the radiolabeled ligand from the receptor. These results demonstrate that representative compounds of the present invention are effective CRF receptor antagonists.

TABLE 7

Representative Compounds Having a $K_i \leq 250$ nM

| Compound | $R_1$ | $R_2$ | $R_3$ | $R_4$ | $R_5$ | X |
|---|---|---|---|---|---|---|
| II-7 | $nC_3H_7$ | dicyclopropylmethyl | $CH_3$ | H | — | 4-Cl-phenyl |
| II-11 | $nC_3H_7$ | dicyclopropylmethyl | H | H | — | 2,4,6-trichlorophenyl |
| II-16 | $nC_3H_7$ | dicyclopropylmethyl | $CH_3$ | H | — | 4-Br-phenyl |
| II-22 | $nC_3H_7$ | dicyclopropylmethyl | H | H | — | 2,4,6-trimethoxyphenyl |
| II-23 | $nC_3H_7$ | dicyclopropylmethyl | H | H | — | 2,6-dimethoxyphenyl |
| II-24 | $nC_3H_7$ | dicyclopropylmethyl | H | H | — | 2,4,6-trimethylphenyl |
| II-25 | $nC_3H_7$ | dicyclopropylmethyl | $CH_3$ | H | — | 2,6-dimethoxyphenyl |
| II-32 | $nC_3H_7$ | dicyclopropylmethyl | $CH_3$ | H | — | 2-Cl-4-methoxyphenyl |
| II-35 | $nC_3H_7$ | dicyclopropylmethyl | H | H | — | 2-Cl-4,6-dimethoxyphenyl |
| II-36 | $nC_3H_7$ | dicyclopropylmethyl | H | H | — | 2-Cl-4,6-dimethoxyphenyl |

TABLE 7-continued

Representative Compounds Having a $K_i \leq 250$ nM

| Compound | $R_1$ | $R_2$ | $R_3$ | $R_4$ | $R_5$ | X |
|---|---|---|---|---|---|---|
| II-39 | $nC_3H_7$ | (isopropyl-dicyclopropyl) | $CH_3$ | H | — | 2-OCH₃, 4-OCH₃ phenyl |
| II-43 | $nC_3H_7$ | (isopropyl-dicyclopropyl) | H | H | — | 2-CH₃, 4-OCH₃ phenyl |
| IV-2 | $nC_3H_7$ | (isopropyl-dicyclopropyl) | — | — | $NH_2$ | 2,4,6-trichlorophenyl |
| IV-7 | $nC_3H_7$ | (isopropyl-dicyclopropyl) | — | — | $NH_2$ | 2,4-dichlorophenyl |
| IV-8 | $nC_3H_7$ | (isopropyl-dicyclopropyl) | — | — | H | 2,4-dichlorophenyl |

EXAMPLE 8

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 µl of a solution of 95% ethanol and mM aqueous hydrochloric acid is added to each well and the resulting suspensions are incubated at −20° C. for 16 to 18 hours. The solution is removed into 1.5 ml Eppendorf tubes and the wells washed with an additional 200 µl of ethanol/aqueous hydrochloric acid and pooled with the first fraction. The samples are lyophilized and then resuspended with 500 µl sodium acetate buffer. The measurement of cAMP in the samples is performed using a single antibody kit from Biomedical Technologies Inc. (Stoughton, MA). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

We claim:

1. A compound represented by structure V or VI:

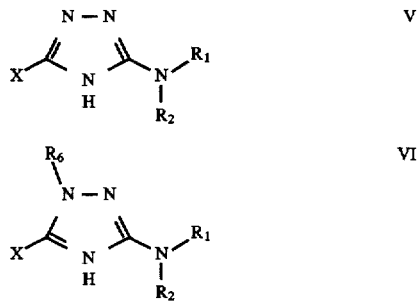

wherein $R_1$ and $R_2$ are independently selected from a $C_1$–$C_6$ alkyl group, a $C_3$–$C_6$ alkenyl group, a $C_2$–$C_6$ alkylether group, a $C_2$–$C_6$ alkylthioether group, a $C_4$–$C_9$ cycloalkylalkyl group, a $C_7$–$C_{20}$ dicycloalkylalkyl group, a $C_7$–$C_{20}$ cycloalkylarylalkly group, a $C_7$–$C_{20}$ arylalkyl group, a $C_7$–$C_{20}$ diarylalkyl group, a $C_3$–$C_4$ heteroaryl group, a $C_3$–$C_4$ heteroarylalkyl group, and substituted derivatives thereof, $R_6$ is selected from hydrogen and methyl; and X is a 2,4-, 2,6-, 2,4,5- or 2,4,6-substituted phenyl group wherein each substituent of the substituted phenyl group is individually selected from a $C_1$–$C_3$ alkyl, a $C_1$–$C_3$ alkoxy, halogen, a $C_1$–$C_3$ thioalkyl group and a $C_2$–$C_3$ haloalkyl.

2. The compound of claim 1 wherein the substituted phenyl group is selected from 2,4-dichlorophenyl, 2,4,6-trichlorophenyl, 2,4-dimethoxyphenyl, 2-bromo-4-methylphenyl, 2-methyl-4-bromophenyl, 2,6-dimethoxy-4-chlorophenyl, 2,4-dimethoxy-6-chlorophenyl, 2,4-dimethyl-6-methoxyphenyl, 2,4-dimethoxy-6-ethoxyphenyl, 2-fluoro-4-methoxyphenyl, 29 46-trimethoxyphenyl, 2,4-dimethoxyphenyl, 2-thiomethyl-4-methoxyphenyl, 2-methyl-4-methoxyphenyl, 2-methoxy-4-methylphenyl, 2-methoxy-4-bromophenyl, 2-fluoro-4-methoxyphenyl, and 2,5-dimethoxy-4-methylphenyl.

3. The compound of claim 1 wherein the substituted phenyl group is selected from 2,4-dichlorophenyl and 2,4,6-trichlorophenyl.

4. The compound of claim 1 wherein the substituted phenyl group is 4-cyano-2,6-dimethylphenyl.

5. The compound of claim 1 wherein the substituted phenyl group is 2,4,6-trimethoxyphenyl, 2-chloro-4,6-dimethoxyphenyl and 4-chloro-2,6-dimethoxyphenyl.

6. The compound of claim 1 wherein at least one of $R_1$ and $R_2$ is a C1–C6 alkyl group.

7. The compound of claim 6 wherein the alkyl group is selected from methyl, ethyl, n-propyl, n-butyl and n-pentyl.

8. The compound of claim 1 wherein at least one of $R_1$ and $R_2$ is selected from a C7–C20 dicycloalkylalkyl group.

9. The compound of claim 8 wherein the dicycloalkylalkyl group is dicyclopropylmethyl.

10. The compound of claim 1 wherein at least one of $R_1$ and $R_2$ is selected from a diarylalkyl group.

11. The compound of claim 10 wherein the diarylalkyl group is diphenylmethyl.

12. The compound of claim 1 wherein $R_1$ is a C1–C6 n-alkyl group and $R_2$ is a C7–C20 dicycloalkylalkyl group.

13. The compound of claim 12 wherein the n-alkyl group is n-propyl and the dicycloalkyl alkyl group is dicyclopropylmethyl.

14. The compound of claim 1 wherein $R_6$ is methyl.

15. A composition comprising a compound of claim 1 in combination with a pharmaceutically acceptable carrier or diluent.

16. The composition of claim 15 wherein the compound is present in the composition in an amount ranging from 0.1 to 250 mg.

17. The composition of claim 15 wherein the compound is present in the composition in an amount ranging from 1 to 60 mg.

18. The composition of claim 15 formulated for systemic administration.

19. The composition of claim 15 formulated for oral administration.

20. The composition of claim 15 formulated for parental administration.

21. A method for antagonizing a CRF receptor in a warm-blooded animal, comprising administering to the animal an effective amount of a compound of claim 1.

22. A method for treating a disorder manifesting hypersecretion of CRF in a warm-blooded animal, comprising administering to the animal an effective amount of a compound of claim 1.

23. The method of claim 22 wherein the disorder is depression.

24. The method of claim 22 wherein the disorder is an anxiety-related disorder.

25. The method of claim 24 wherein the anxiety-related disorder is a generalized anxiety disorder.

26. The method of claim 24 wherein the anxiety-related disorder is panic disorder.

27. The method of claim 24 wherein the anxiety-related disorder is obsessive-compulsive disorder.

28. The method of claim 24 wherein the anxiety-related disorder is abnormal aggression.

29. The method of claim 24 wherein the anxiety-related disorder is a cardiovascular disorder.

30. The method of claim 29 wherein the cardiovascular disorder is unstable angina.

31. The method of claim 29 wherein the cardiovascular disorder is reactive hypertension.

32. The method of claim 29 wherein the disorder is a feeding disorder.

33. The method of claim 32 wherein the feeding disorder is anorexia nervosa.

34. The method of claim 32 wherein the feeding disorder is bulimia.

35. The method of claim 32 wherein the feeding disorder is irritable bowel syndrome.

36. The method of claim 22 wherein the disorder is stress-induced immune suppression.

37. The method of claim 22 wherein the disorder is stroke.

38. The method of claim 22 wherein the disorder is Cushing's disease.

39. The method of claim 22 wherein the disorder is infantile spasms.

40. The method of claim 22 wherein the disorder is epilepsy.

41. The method of claim 22 wherein the disorder is seizure.

42. The method of claim 22 wherein the disorder is substance abuse.

43. The method of claim 22 wherein the disorder is substance withdrawal.

44. A method for treating an inflammatory condition in a warm-blooded animal, comprising administering to the warm-blooded animal an effective amount of a compound of claim 1.

45. The method of claim 44 wherein the inflammatory condition is rheumatoid arthritis.

46. The method of claim 44 wherein the inflammatory condition is uveitis.

47. The method of claim 44 wherein the inflammatory condition is asthma.

48. The method of claim 44 wherein the inflammatory condition is inflammatory bowel disease.

49. The method of claim 44 wherein the inflammatory condition is G.I. motility.

50. A method for treating an inflammatory condition in a warm-blooded animal, comprising administering to the warm-blooded animal an effective amount of a compound represented by structure V or VI:

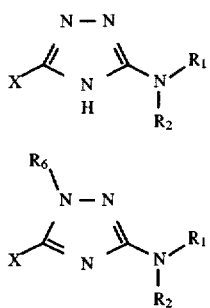

wherein the inflammatory condition is selected from rheumatoid arthritis, uveitis, asthma, inflammatory bowel disease and G.I. motility, and wherein $R_1$ and $R_2$ are independently selected from a $C_1$–$C_6$ alkyl group, a $C_3$–$C_6$ alkenyl group, a $C_2$–$C_6$ alkylether group, a $C_2$–$C_6$ alkylthioether group, a $C_4$–$C_9$ cycloalkylalkyl group, a $C_7$–$C_{20}$ dicycloalkylalkyl group, a $C_7$–$C_{20}$ cycloalkylarylalkly group, a $C_7$–$C_{20}$ arylalkyl group, a $C_7$–$C_{20}$ diarylalkyl group, a $C_3$–$C_4$ heteroaryl group, a $C_3$–$C_4$ heteroarylalkyl group, and substituted derivatives thereof;

$R_6$ is selected from hydrogen and methyl; and

X is a 4-, 2,4-, 2,6-, 2,4,5- or 2,4,6-substituted phenyl group.

51. The method of claim 50 wherein the inflammatory condition is uveitis.

52. The method of claim 50 wherein the inflammatory condition is asthma.

53. The method of claim 50 wherein the inflammatory condition is inflammatory bowel disease.

54. The method of claim 50 wherein the inflammatory condition is G.I. motility.

\* \* \* \* \*

UNITED STATES PATENT AND TRADEMARK OFFICE
CERTIFICATE OF CORRECTION

PATENT NO. : 5,795,905

DATED : August 18, 1998

INVENTOR(S) : James R. McCarthy et al.

It is certified that error appears in the above-identified patent and that said Letters Patent is hereby corrected as shown below:

On the Title Page, Item '[75] Inventors' section on the front cover

--Dimitri E. Grigoriadis, Carlsbad, CA; Raymond Dagnino, Jr., San Diego, CA; Charles Q. Huang, San Diego, CA; Zhengyu Liu, San Diego, CA--.

Claim 1, column 61, lines 2-3, "a $C_3$ - $C_4$ heteroaryl group" should read --a $C_3$ - $C_{14}$ heteroaryl group--.

Claim 1, column 61, line 3, "a $C_3$ - $C_4$ heteroarylalkyl group" should read --a $C_3$ - $C_{14}$ heteroarylalkyl group--.

Claim 2, column 61, line 17, "29 46-trimethoxyphenyl" should read --2,4,6-trimethoxyphenyl--.

Claim 50, column 64, lines 3-4, "a $C_3$ - $C_4$ heteroaryl group" should read --a $C_3$ - $C_{14}$ - heteroaryl group--.

Claim 50, column 64, line 4, "a $C_3$ - $C_{14}$ heteroarylalkyl group" should read --a $C_3$ - $C_{14}$ heteroarylalkyl group--.

Signed and Sealed this

Tenth Day of April, 2001

*Attest:*

NICHOLAS P. GODICI

*Attesting Officer*     *Acting Director of the United States Patent and Trademark Office*